(12) United States Patent  
Tanaka

(10) Patent No.: US 10,204,401 B2
(45) Date of Patent: Feb. 12, 2019

(54) IMAGE PROCESSING APPARATUS AND METHOD, AND NON-TRANSITORY COMPUTER READABLE MEDIUM

(71) Applicant: FUJIFILM Corporation, Tokyo (JP)

(72) Inventor: Yasutake Tanaka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 44 days.

(21) Appl. No.: 15/497,580

(22) Filed: Apr. 26, 2017

(65) Prior Publication Data

US 2017/0365043 A1 Dec. 21, 2017

(30) Foreign Application Priority Data

Jun. 21, 2016 (JP) .................... 2016-122344

(51) Int. Cl.
```
G06T 5/00      (2006.01)
H04N 1/401     (2006.01)
H04N 1/409     (2006.01)
G01N 21/64     (2006.01)
```
(52) U.S. Cl.
CPC ............. *G06T 5/002* (2013.01); *H04N 1/401* (2013.01); *H04N 1/409* (2013.01); *G01N 21/6456* (2013.01); *G06T 2207/10064* (2013.01); *G06T 2207/30004* (2013.01); *H04N 2201/0079* (2013.01)

(58) Field of Classification Search
USPC .................................. 382/128, 275
See application file for complete search history.

(56) References Cited

U.S. PATENT DOCUMENTS

| | | | | |
|---|---|---|---|---|
| 4,551,626 A * | 11/1985 | Agano | ................... | G01T 1/2014 250/347 |
| 6,806,486 B2 * | 10/2004 | Isoda | ................... | G01T 1/2014 250/584 |
| 6,996,289 B1 * | 2/2006 | Tsutamori | ............. | H04N 1/401 348/241 |
| 7,100,831 B2 * | 9/2006 | Nishioka | ................. | H04N 1/40 235/462.25 |
| 7,580,589 B2 * | 8/2009 | Bosco | ...................... | G06T 5/20 382/260 |

(Continued)

OTHER PUBLICATIONS

Extended European Search Report, dated Oct. 6, 2017, for corresponding European Application No. 17168071.3.

*Primary Examiner* — Ishrat I Sherali
(74) *Attorney, Agent, or Firm* — Birch, Stewart, Kolasch & Birch, LLP

(57) ABSTRACT

There is provided an image processing apparatus, method, and operation program capable of appropriately removing an abnormal pixel even in a case where the abnormal pixel is present in a tailing region. An abnormal pixel removing section removes an abnormal pixel from an image in which tailing and the dot-shaped abnormal pixel are mixed every other line. The abnormal pixel removing section selects neighboring pixels from only odd lines or even lines including a line, in which a target pixel to be corrected is present, depending on whether or not the line in which the target pixel is present is an odd-numbered line in a sub-scanning direction, and performs processing for removing the abnormal pixel based on the selected neighboring pixels.

10 Claims, 22 Drawing Sheets

(56) References Cited

U.S. PATENT DOCUMENTS

| | | | |
|---|---|---|---|
| 8,013,914 B2* | 9/2011 | Egawa | H04N 5/367 |
| | | | 348/241 |
| 2003/0219170 A1* | 11/2003 | Ishido | H04N 1/193 |
| | | | 382/275 |
| 2004/0125420 A1* | 7/2004 | Tsutsumi | H04N 1/00002 |
| | | | 358/498 |
| 2012/0183123 A1* | 7/2012 | Tada | G01N 23/046 |
| | | | 378/62 |
| 2016/0084966 A1 | 3/2016 | Reiser et al. | |

* cited by examiner

FIG. 11
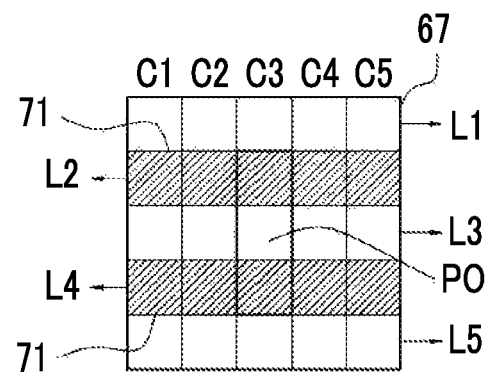
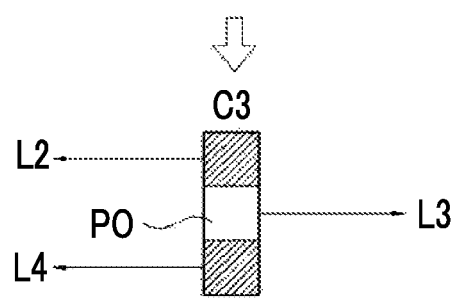
SKIP S203 BECAUSE OF N IN S202
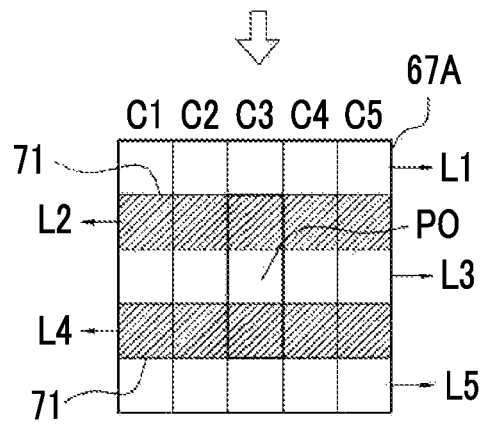

FIG. 13
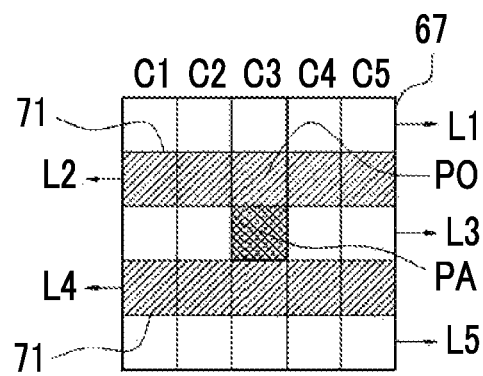
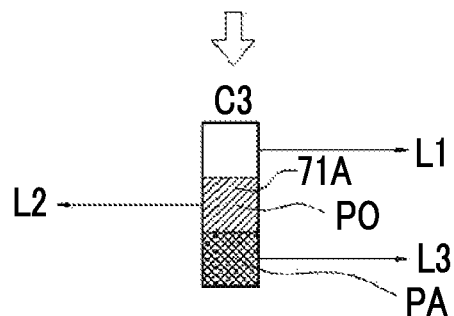
SKIP S203 BECAUSE OF N IN S202
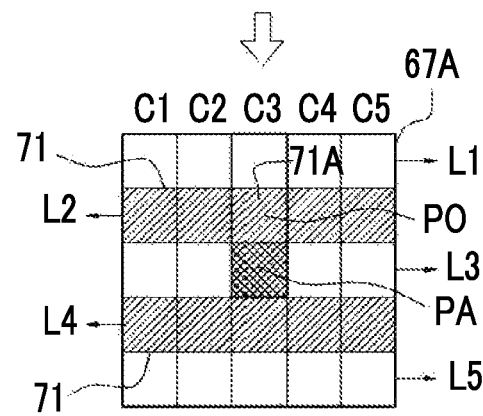

IMAGE PROCESSING APPARATUS AND METHOD, AND NON-TRANSITORY COMPUTER READABLE MEDIUM

CROSS-REFERENCE TO RELATED APPLICATION

This application claims priority under 35 USC 119 from Japanese Patent Application No. 2016-122344, filed 21 Jun. 2016, the disclosure of which is incorporated by reference herein.

BACKGROUND OF THE INVENTION

1. Field of the Invention

The present invention relates to an image processing apparatus and method, and non-transitory computer readable medium.

2. Description of the Related Art

A fluorescence image detection system is known that detects a fluorescence image of an image carrier, in which a biological substance such as a gene is labeled with a fluorescent dye, by emitting excitation light to the image carrier and receiving the fluorescence emitted from the fluorescent dye (JP2003-319147A corresponding to U.S. Pat. No. 7,100,831, and JP2001-069353A corresponding to U.S. Pat. No. 6,996,289).

As disclosed in JP2003-319147A, a fluorescence image detection system may adopt a reciprocating scanning type image reading apparatus, in which an optical head for reading an image reciprocates in the main scanning direction, as a scanning system for an image of an image carrier. In the reciprocating scanning method, the scanning direction is reversed every one line. For example, the optical head moves from right to left in the odd line, and the optical head moves from left to right in the next even line. Here, the odd line and the even line are lines extending in the main scanning direction, and an odd-numbered line in the sub-scanning direction perpendicular to the main scanning direction is referred to as an odd line and an even-numbered line in the sub-scanning direction perpendicular to the main scanning direction is referred to as an even line.

The reciprocating scanning method referred to herein is a reciprocating scanning method in a narrow sense in which an image is read by each of forward scanning and backward scanning of the optical head and each image read by forward scanning and backward scanning is treated as an image for one line. In the reciprocating scanning method in a narrow sense, for example, in a case where the forward scanning is for the odd line, the backward scanning is for the even line. That is, the scanning direction is reversed every one line. Accordingly, each image read by alternately reversing the scanning direction is treated as an image for one line, and an image for one screen is generated with an image of each line as a constituent component.

The reciprocating scanning method broadly includes the following two methods in addition to the reciprocating scanning method in the narrow sense. In the first method, the optical head is reciprocated, but only forward scanning is performed for image reading and the optical head is just returned to the initial position in the main scanning direction. That is, in the return path, image reading is not performed. In this method, all images of respective lines, which are constituent components of an image for one screen, are images read by forward scanning. Eventually, this method can be said to be a method of reading an image for one line by one-time reciprocation of the optical head.

In the other method, similarly to the reciprocating scanning method in a narrow sense, scanning is performed in both forward scanning and backward scanning, and an image for one line is read by each scanning. However, an image obtained by adding images for two lines read by the forward scanning and the backward scanning is treated as an image for one line. In this method, images are read by the forward scanning and the backward scanning, but these are added. Eventually, this method can be said to be a method of reading an image for one line by one-time reciprocation of forward scanning and backward scanning. Hereinafter, only the reciprocating scanning method in a narrow sense will be described, and the reciprocating scanning method in a narrow sense is simply referred to as a reciprocating scanning method.

As disclosed in JP2003-319147A, in the case of using an optical head for photoelectrically reading an image, such as a photomultiplier, tailing may occur in the read image assuming that there is a boundary with a large density difference on the image carrier to be imaged. Tailing occurs, for example, in a case where scanning is performed from a high density region to a low density region. More specifically, the tailing extends in a stripe shape in the main scanning direction from the high density region to the low density region at the boundary between the high density region and the low density region. In the reciprocating scanning method, tailing occurs every other line and becomes a stripe shape.

This is because, in the reciprocating scanning method, the scanning direction in the main scanning direction is different every line, and therefore, tailing occurs, for example, in a case where the optical head performs scanning across the boundary from the high density region to the low density region in the odd line. However, in the next even line, the scanning direction of the optical head is reversed. Accordingly, since the same boundary is scanned in the opposite direction from the low density region to the high density region, tailing does not occur.

In the apparatus disclosed in JP2003-319147A, for the stripe-shaped tailing extending in the main scanning direction, correction to make the tailing not noticeable is made by performing smoothing in the sub-scanning direction perpendicular to the main scanning direction.

JP2001-069353A discloses abnormal pixel removal processing for removing an abnormal pixel based on the pixel values of neighboring pixels around the abnormal pixel in a case where a dot-shaped abnormal pixel generated as a high-density significant point is present in the read image. As neighboring pixels, adjacent pixels around the abnormal pixel are selected. Since the abnormal pixel is a significant point, neighboring pixels adjacent to the abnormal pixel have low density. Therefore, by correcting the pixel value of the abnormal pixel (decreasing the density) according to the pixel values of neighboring pixels, it is possible to remove the abnormal pixel.

However, in a case where the abnormal pixel disclosed in JP2001-069353A is present in a tailing region including a plurality of tailings disclosed in JP2003-319147A, there is a problem that the abnormal pixel cannot be appropriately removed in the method disclosed in JP2001-069353A.

This is because, in a case where an abnormal pixel is present in the tailing region, neighboring pixels adjacent to the abnormal pixel include pixels forming the tailing. In a case where the neighboring pixels are pixels forming the tailing, the density of the neighboring pixels is high. Even assuming that the abnormal pixel is corrected using high-density neighboring pixels, the density of the abnormal pixel remains high. Accordingly, it is not possible to appropriately remove the abnormal pixel. In other words, in a case where an abnormal pixel is present in the tailing region, there is a problem that the abnormal pixel cannot be appropriately removed due to the influence of the tailing.

SUMMARY OF THE INVENTION

It is an object of the invention to provide an image processing apparatus and method, and non-transitory computer readable medium capable of appropriately removing an abnormal pixel even in a case where the abnormal pixel is present in a tailing region.

In order to solve the aforementioned problem, an image processing apparatus of the invention is an image processing apparatus that uses a scanning unit that performs scanning for image reading on an image carrier carrying image information by moving an optical head relative to the image carrier and that reads a one-dimensional line image in a main scanning direction line by line by performing reciprocating scanning, in which forward scanning and backward scanning are alternately repeated for each line in the main scanning direction, and reads a two-dimensional image by performing scanning in a sub-scanning direction perpendicular to the main scanning direction in combination with the reciprocating scanning, acquires the two-dimensional image from the scanning unit, and performs image processing on the two-dimensional image. The image processing apparatus comprises an abnormal pixel removing unit and a tailing removing unit. The abnormal pixel removing unit removes a dot-shaped abnormal pixel present in the two-dimensional image based on neighboring pixels present around the abnormal pixel. The abnormal pixel removing unit selects the neighboring pixels from only at least one odd line including an odd line, in which a target pixel to be corrected in order to remove the abnormal pixel is present, in a case where a line in which the target pixel is present is an odd-numbered line in the sub-scanning direction and selects the neighboring pixels from only at least one even line including an even line, in which the target pixel is present, in a case where a line in which the target pixel is present is an even-numbered line in the sub-scanning direction, and removes the abnormal pixel based on the selected neighboring pixels. The tailing removing unit removes stripe-shaped tailing, which occurs every other line due to the reciprocating scanning in the two-dimensional image and extends in the main scanning direction, from the two-dimensional image.

It is preferable to perform tailing removal processing for removing the tailing after performing abnormal pixel removal processing for removing the abnormal pixel.

It is preferable that, in the abnormal pixel removal processing for removing the abnormal pixel, the number of lines for selecting the neighboring pixels is two or more.

It is preferable that, in the abnormal pixel removal processing for removing the abnormal pixel, the lines for selecting the neighboring pixels include at least an n-th line, an (n−2)-th line, and an (n+2)-th line in a case where the line in which the target pixel is present is the n-th line (where n is an integer of 1 or more).

It is preferable that, in the abnormal pixel removal processing, in a case where the line in which the target pixel is present is an end line located in an upper end portion or a lower end portion of the two-dimensional image in the sub-scanning direction, the abnormal pixel removing unit performs end portion processing in which a virtual line is additionally set at an upper end or a lower end of the two-dimensional image and the virtual line is used as the line for selecting the neighboring pixels.

It is preferable that the tailing removing unit performs tailing determination processing in which a pixel value of the target pixel is compared with pixel values of upper and lower pixels adjacent to the target pixel in the sub-scanning direction and the target pixel is determined to be a tailing pixel forming the tailing in a case where the pixel value of the target pixel is higher than the pixel values of the upper and lower pixels and a difference or a ratio between the pixel value of the target pixel and the pixel values of the upper and lower pixels is equal to or greater than a predetermined value.

It is preferable that, in the tailing determination processing, for a plurality of columns including a column, which extends in the sub-scanning direction and in which the target pixel is present, and left and right columns adjacent to the target pixel in the main scanning direction, the tailing removing unit compares pixel values between pixels adjacent to each other in the sub-scanning direction and uses a result of the comparison for tailing determination.

It is preferable that the image carrier contains a sample that emits fluorescence and that the scanning unit has an excitation light source that generates excitation light to be emitted to the image carrier and an optical sensor that photoelectrically converts fluorescence that is excited by the excitation light and is received by the optical head.

An image processing method of the invention is an image processing method in which a scanning unit, which performs scanning for image reading on an image carrier carrying image information by moving an optical head relative to the image carrier and which reads a one-dimensional line image in a main scanning direction line by line by performing reciprocating scanning, in which forward scanning and backward scanning are alternately repeated for each line in the main scanning direction, and reads a two-dimensional image by performing scanning in a sub-scanning direction perpendicular to the main scanning direction in combination with the reciprocating scanning, is used, the two-dimensional image is acquired from the scanning unit, and image processing is performed on the two-dimensional image. The image processing method comprises an abnormal pixel removing step and a tailing removing step. In the abnormal pixel removing step, a dot-shaped abnormal pixel present in the two-dimensional image is removed based on neighboring pixels present around the abnormal pixel. The neighboring pixels are selected from only at least one odd line including an odd line, in which a target pixel to be corrected in order to remove the abnormal pixel is present, in a case where a line in which the target pixel is present is an odd-numbered line in the sub-scanning direction, and the neighboring pixels are selected from only at least one even line including an even line, in which the target pixel is present, in a case where a line in which the target pixel is present is an even-numbered line in the sub-scanning direction, and the abnormal pixel is removed based on the selected neighboring pixels. In the tailing removing step, stripe-shaped tailing, which occurs every other line due to the reciprocating scanning in the two-dimensional image and extends in the main scanning direction, is removed from the two-dimensional image.

A non-transitory computer readable medium for storing a computer-executable program is provided, the computer-executable program being for execution of image processing that uses a scanning unit that performs scanning for image reading on an image carrier carrying image information by moving an optical head relative to the image carrier and that reads a one-dimensional line image in a main scanning direction line by line by performing reciprocating scanning, in which forward scanning and backward scanning are alternately repeated for each line in the main scanning direction, and reads the two-dimensional image by performing scanning in a sub-scanning direction perpendicular to the main scanning direction in combination with the reciprocating scanning, acquires the two-dimensional image from the scanning unit, and performs image processing on the two-dimensional image. The computer-executable program includes an abnormal pixel removing step and a tailing removing step. In the abnormal pixel removing step, a dot-shaped abnormal pixel present in the two-dimensional image is removed based on neighboring pixels present around the abnormal pixel. The neighboring pixels are selected from only at least one odd line including an odd line, in which a target pixel to be corrected in order to remove the abnormal pixel is present, in a case where a line in which the target pixel is present is an odd-numbered line in the sub-scanning direction, and the neighboring pixels are selected from only at least one even line including an even line, in which the target pixel is present, in a case where a line in which the target pixel is present is an even-numbered line in the sub-scanning direction, and the abnormal pixel is removed based on the selected neighboring pixels. In the tailing removing step, stripe-shaped tailing, which occurs every other line due to the reciprocating scanning in the two-dimensional image and extends in the main scanning direction, is removed from the two-dimensional image.

According to the invention, even in a case where an abnormal pixel is present in a tailing region, it is possible to appropriately remove the abnormal pixel.

BRIEF DESCRIPTION OF THE DRAWINGS

FIG. 11 is an image transition diagram of tailing removal processing in a case where a target pixel is not a tailing pixel.
FIG. 13 is an image transition diagram in the case of performing tailing removal processing on a tailing image including an abnormal pixel.

DESCRIPTION OF THE PREFERRED EMBODIMENTS

First Embodiment

Figure 1:
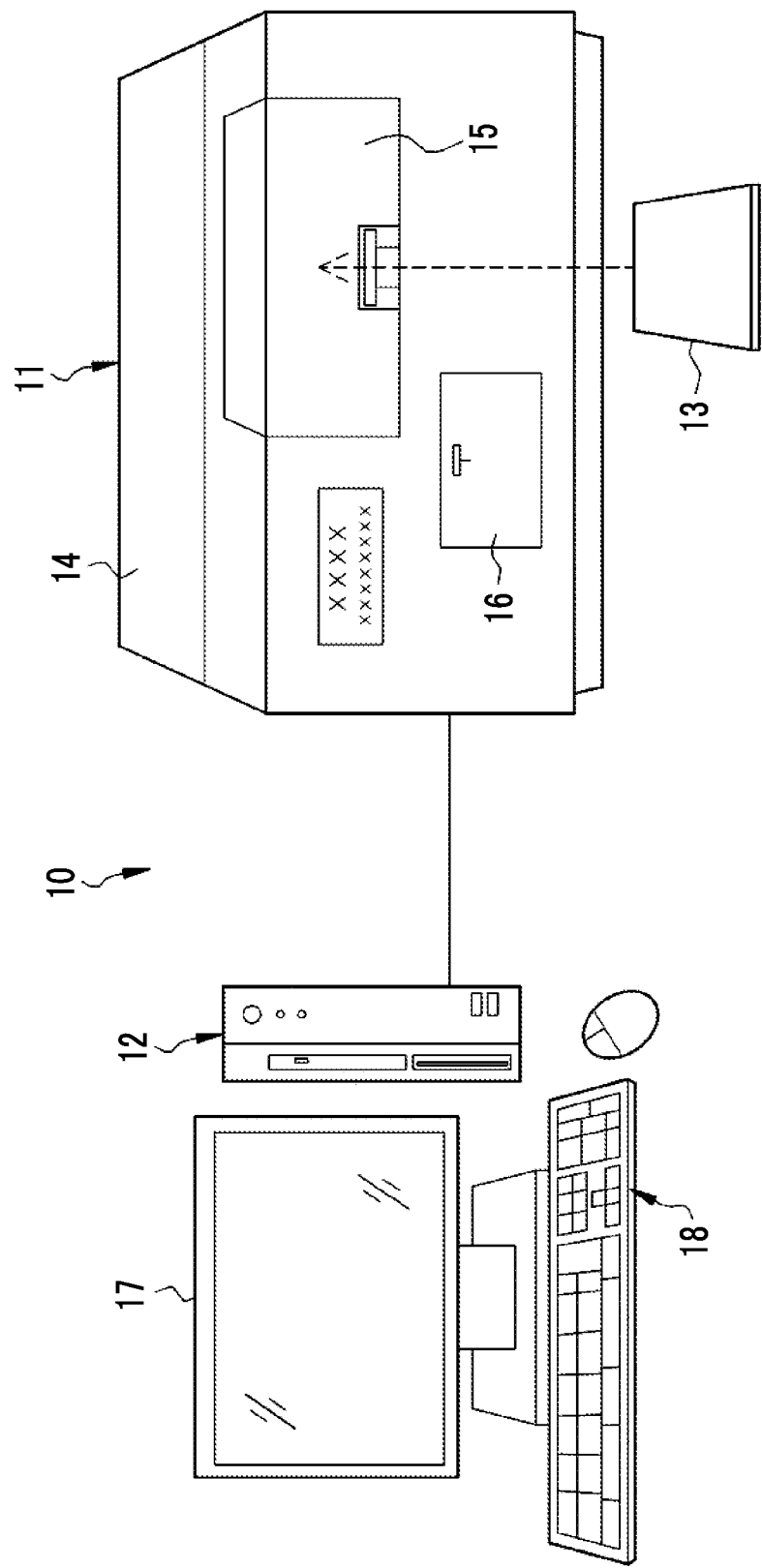
FIG. 1 is a diagram showing an image detection system.

In FIG. 1, an image detection system 10 includes an image reading apparatus 11 and a console 12 corresponding to a control device of the image reading apparatus 11. The image reading apparatus 11 and the console 12 are connected to each other by, for example, a communication cable conforming to the universal serial bus (USB) standard, so that transmission and reception of data therebetween are possible.

The image reading apparatus 11 detects light DL (refer to FIG. 2 or the like) from an image carrier 13 carrying image information, and outputs an image of the image carrier 13 based on the detected light DL. The image carrier 13 contains a biological substance, such as deoxyribonucleic acid (DNA), ribonucleic acid (RNA), or protein, as a sample, and is a gel support or a transfer support on which an electrophoretic pattern of the biological substance is recorded.

A biological substance is labeled by adding a fluorescent dye. In the case of using a fluorescent dye, the light DL detected from the image carrier 13 is fluorescence emitted from the fluorescent dye. There is a plurality of kinds of fluorescent dyes, and excitation wavelengths and emission wavelengths thereof are different. For example, there are a fluorescent dye that is excited by blue excitation light and emits blue fluorescence having a longer wavelength than the blue excitation light, a fluorescent dye that is excited by green excitation light and emits green fluorescence having a longer wavelength than the green excitation light, a fluorescent dye that is excited by red excitation light and emits red fluorescence having a longer wavelength than the red excitation light, and the like. In addition to using the fluorescent dye as a sample, for example, a fluorescent protein that obtains fluorescence by gene expression may be used.

The entire image reading apparatus 11 is covered with a housing 14. The inside of the image reading apparatus 11 is shielded from external light, which becomes noise in the detection of the light DL, by the housing 14. On the front surface of the housing 14, an openable and closable lid 15 for setting the image carrier 13 in the image reading apparatus 11 is provided. Reference numeral 16 is an openable and closable lid for replacing a filter unit 30 (refer to FIG. 2).

The console 12 is, for example, a desktop type personal computer, and has a display 17 and an operation unit 18 configured to include a keyboard and a mouse. The display 17 displays a screen used for the operation of the operation unit 18 in addition to an image. The operation screen forms a graphical user interface (GUI). The console 12 receives an input of an operation instruction from the operation unit 18 through the operation screen of the display 17.

Figure 2:
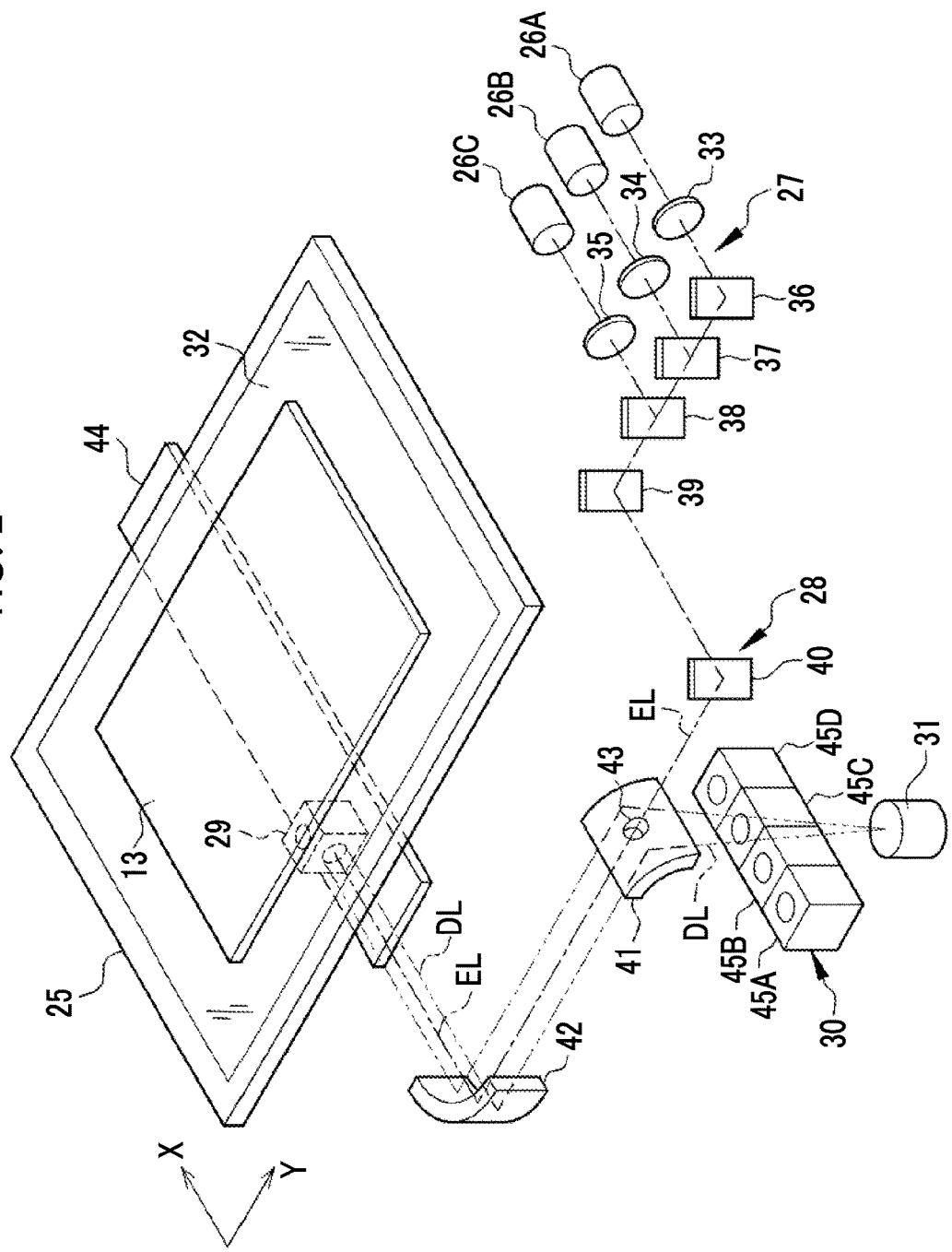
FIG. 2 is a schematic diagram of an image reading apparatus.

In FIG. 2, a stage 25, excitation light sources 26A, 26B, and 26C, a light source optical system 27, a light guiding optical system 28, an optical head 29, a filter unit 30, and a photomultiplier 31 are provided in the image reading apparatus 11.

The stage 25 holds the image carrier 13. The stage 25 has a rectangular frame shape, and a transparent glass plate 32 is fitted in the frame. The image carrier 13 is placed on the glass plate 32.

The excitation light sources 26A to 26C emit excitation light EL of a fluorescent dye. In order to correspond to a plurality of kinds of fluorescent dyes, the excitation light sources 26A to 26C having different emission wavelength bands for the excitation light EL are prepared.

Specifically, the excitation light source 26A emits red excitation light having a center wavelength of 635 nm, the excitation light source 26B emits green excitation light having a center wavelength of 532 nm, and the excitation light source 26C emits blue excitation light having a center wavelength of 488 nm. The excitation light sources 26A and 26C are formed by, for example, semiconductor lasers, and the excitation light source 26B is formed by, for example, a second harmonic generation element. The emission wavelength band of the excitation light EL is not limited thereto. The number of excitation light sources is not limited to three, and one excitation light source may be used or four or more excitation light sources may be used.

The light source optical system 27 is configured to include collimator lenses 33, 34, and 35, mirrors 36 and 39, and dichroic mirrors 37 and 38. The collimator lenses 33 to 35 are arranged on the front surfaces of the excitation light sources 26A to 26C, respectively, and convert excitation light beams of respective colors emitted from the excitation light sources 26A to 26C into parallel beams. The mirror 36 reflects red excitation light converted into parallel light by the collimator lens 33 toward the dichroic mirror 37.

The dichroic mirror 37 transmits the red excitation light from the mirror 36, and reflects green excitation light converted into parallel light by the collimator lens 34 toward the dichroic mirror 38. The dichroic mirror 38 transmits the red excitation light from the mirror 36 and the green excitation light from the dichroic mirror 37, and reflects blue excitation light converted into parallel light by the collimator lens 35 toward the dichroic mirror 39.

The mirror 39 reflects, toward the light guiding optical system 28, the red excitation light that is reflected by the mirror 36 and is transmitted through the dichroic mirrors 37 and 38, the green excitation light that is reflected by the dichroic mirror 37 and is transmitted through the dichroic mirror 38, and the blue excitation light that is reflected by the dichroic mirror 38.

The light guiding optical system 28 is configured to include a mirror 40, a holed concave mirror 41, and a concave mirror 42. The mirror 40 reflects the excitation light EL from the mirror 39 of the light source optical system 27 toward the holed concave mirror 41. The holed concave mirror 41 has a through hole 43 in a central portion. The excitation light EL from the mirror 40 passes through the through hole 43 and travels toward the concave mirror 42. The concave mirror 42 reflects the excitation light EL having passed through the through hole 43 toward the optical head 29.

The light DL from the optical head 29 is incident on the concave mirror 42. The concave mirror 42 reflects the light DL toward the holed concave mirror 41. The holed concave mirror 41 reflects the light DL from the concave mirror 42 toward the filter unit 30. In this manner, the holed concave mirror 41 transmits the excitation light EL therethrough using the through hole 43 and reflects the light DL toward the filter unit 30, thereby branching the optical paths of the excitation light EL and the light DL.

The optical head 29 moves relative to the reading surface, which is a two-dimensional plane of the image carrier 13 in the X and Y directions, to perform scanning for reading the two-dimensional image. Specifically, the optical head 29 emits the excitation light EL to the image carrier 13 and captures the light DL from the image carrier 13 while moving relative to the image carrier 13. The optical head 29 moves in a main scanning direction X and a sub-scanning direction Y to scan the entire surface of the reading surface.

Figure 3:
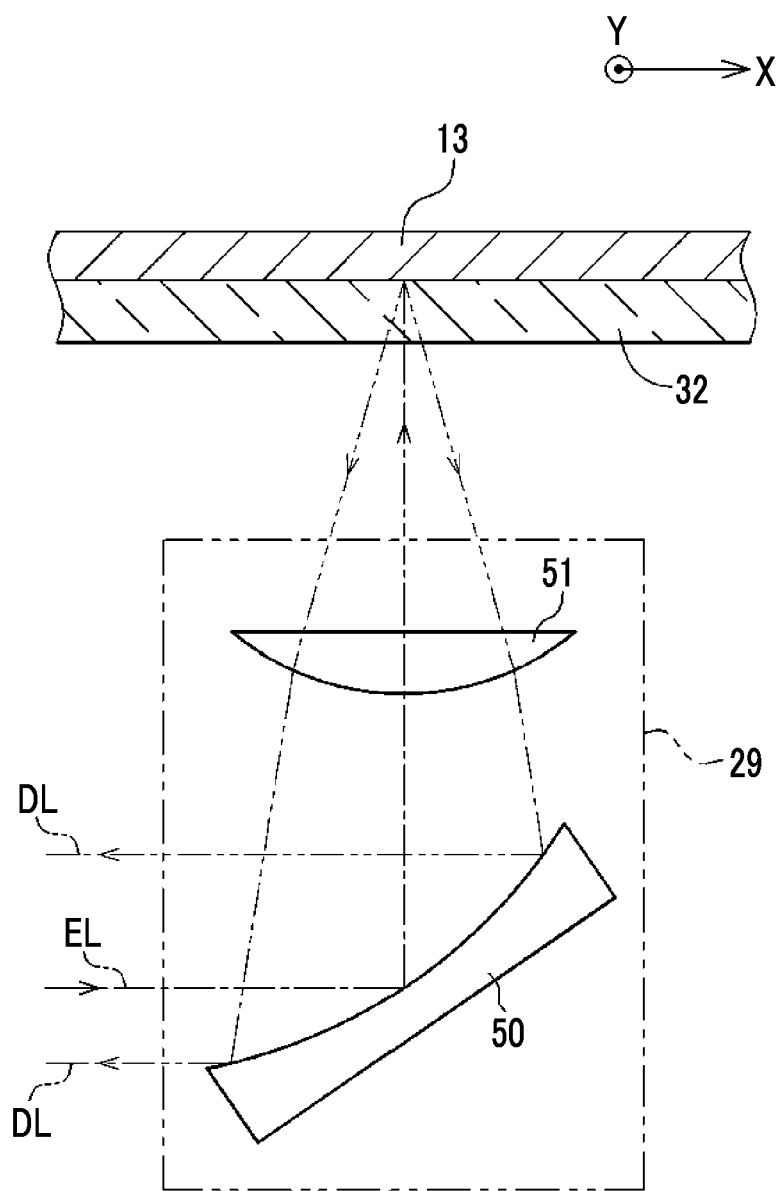
FIG. 3 is a schematic diagram of an optical head.

As shown in FIG. 3, a concave mirror 50 and an aspheric lens 51 are mounted in the optical head 29. The concave mirror 50 reflects the excitation light EL, which is incident from the concave mirror 42 of the light guiding optical system 28, toward the aspheric lens 51. The aspheric lens 51 condenses the excitation light EL from the concave mirror 50 onto the back surface of the image carrier 13 placed on the glass plate 32. In addition, the aspheric lens 51 condenses the light DL that is emitted from the image carrier 13 by the emission of the excitation light EL thereto, and makes the light DL incident on the concave mirror 50. The concave mirror 50 further condenses the light DL from the aspheric lens 51, and makes the light DL incident on the concave mirror 42 of the light guiding optical system 28 as substantially parallel light.

Although not shown in the diagrams, an adjustment mechanism such as a beam expander or a beam reducer for adjusting the diameter of the excitation light EL to be emitted to the back surface of the image carrier 13 may be mounted in the optical head 29.

In FIG. 2, the filter unit 30 is located on the optical path of the light DL between the holed concave mirror 41 and the photomultiplier 31. The filter unit 30 is configured to include four filters 45A, 45B, 45C, and 45D arranged in the sub-scanning direction Y.

The filter unit 30 is movable in the main scanning direction X by a motor, a rail, or the like (not shown). Accordingly, any one of the filters 45A to 45D is selectively disposed between the holed concave mirror 41 and the photomultiplier 31. For example, any one of the filters 45A to 45C is disposed between the holed concave mirror 41 and the photomultiplier 31 in a case where the image carrier 13 is a gel support or a transfer support, and the filter 45D is disposed between the holed concave mirror 41 and the photomultiplier 31 in a case where the image carrier 13 is a stimulable phosphor sheet.

The light DL from the image carrier 13 contains the excitation light EL although the amount of excitation light EL is small. The excitation light EL is noise that is not necessary for generating an image. Therefore, the filters 45A to 45D have characteristics of cutting the excitation light EL and transmitting the light DL.

Similarly to the excitation light sources 26A to 26C, in order to correspond to a plurality of kinds of fluorescent dyes, the filters 45A to 45C having different emission wavelength bands are prepared. Specifically, the filter 45A cuts light (red excitation light) having a wavelength of 635 nm or less, and transmits light (red fluorescence) having a wavelength longer than 635 nm. Specifically, the filter 45B cuts light (green excitation light) having a wavelength of 532 nm or less, and transmits light (green fluorescence) having a wavelength longer than 532 nm. Specifically, the filter 45C cuts light (blue excitation light) having a wavelength of 488 nm or less, and transmits light (blue fluorescence) having a wavelength longer than 488 nm.

Similarly to the emission wavelength band of the excitation light EL, the transmission wavelength band of the filter is not limited thereto. The number of filters is not limited to four, and may be one or may be five or more.

The light DL transmitted through the filters 45A to 45D is incident on the photomultiplier 31. The photomultiplier 31 photoelectrically detects the received light DL at a predetermined timing, and outputs an analog image signal corresponding thereto. As well known, the photomultiplier 31 is one of optical sensors that photoelectrically convert light into electrical signal.

The photomultiplier 31 has a structure in which a cathode (photoelectric surface) for converting light into electrons, a focusing electrode, an electron multiplying electrode, and an anode for collecting electrons are housed in a vacuum container. In the event that light is incident on the photoelectric surface, photoelectrons are emitted, and the emitted photoelectrons are accelerated and collide with the electron multiplying electrode to generate secondary electrons. This occurs in a cascade manner one after another, so that a signal current (analog image signal) is output. The sensitivity of the photomultiplier 31 changes according to the applied voltage. In this manner, the light DL detected by the optical head 29 is input to the photomultiplier 31, and the photomultiplier 31 outputs an analog image signal corresponding to the input light DL. As a result, an image is read.

Figure 4:
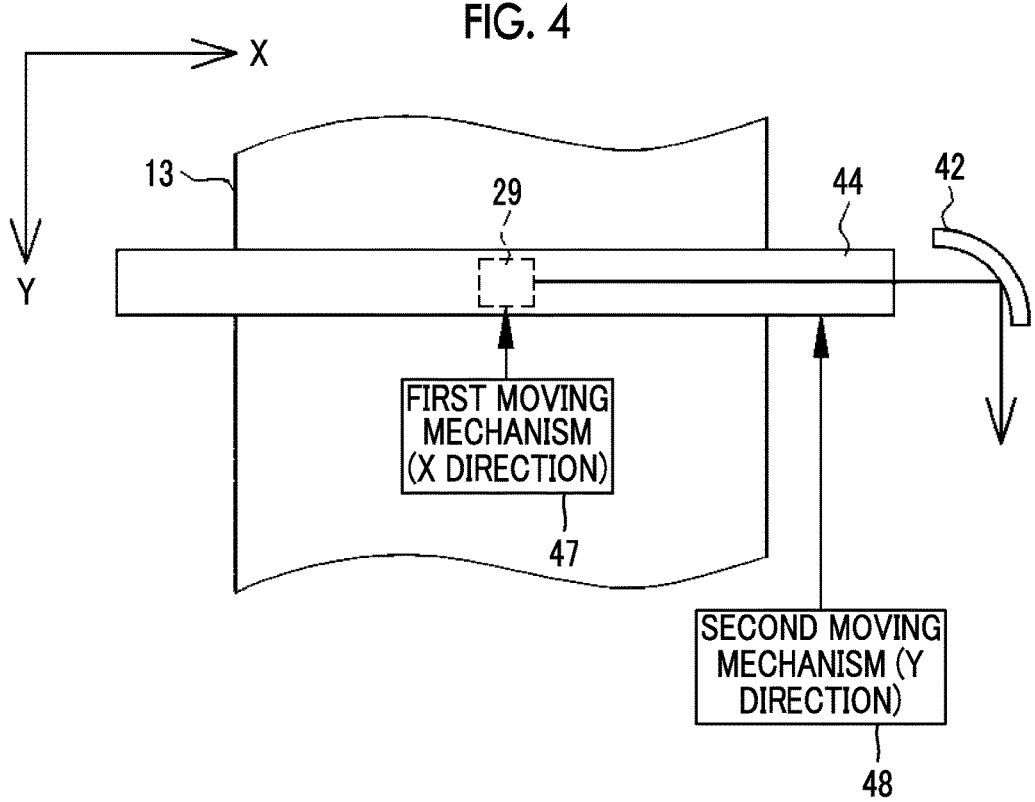
FIG. 4 is an explanatory diagram of a moving mechanism for reciprocating scanning.
Figure 5:
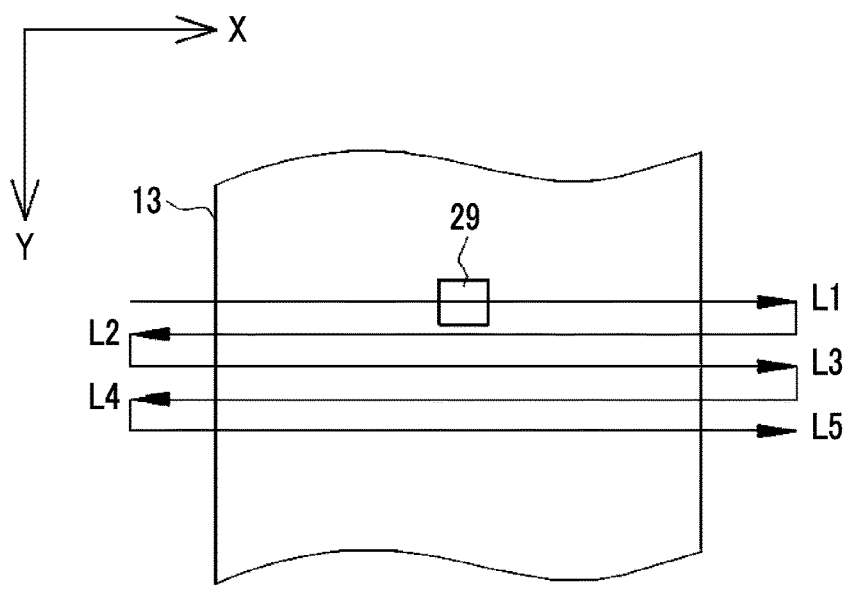
FIG. 5 is an explanatory diagram of the trajectory of the movement of an optical head.

As shown in FIGS. 4 and 5, the optical head 29 adopts a reciprocating scanning method, in which reciprocating scanning is performed in the main scanning direction X, as a scanning method for image reading. The reciprocating scanning method is a scanning method in which forward scanning and backward scanning are alternately repeated for each line in the main scanning direction X.

As described above, the reciprocating scanning method which is the subject of the invention, is a reciprocating scanning method in a narrow sense in which an image is read by each of forward scanning and backward scanning of the optical head and each image read by forward scanning and backward scanning is treated as an image for one line. In the reciprocating scanning method, since the image for one line is read by each of the forward scanning and the backward scanning, there is an advantage that the reading speed of an image for one screen is improved.

As shown in FIGS. 2 and 4, the optical head 29 is disposed on a substrate 44 in the form of an elongated plate provided below the stage 25. The substrate 44 extends in the main scanning direction X, and the optical head 29 reciprocates on the substrate 44 along the main scanning direction X.

As shown in FIG. 4, the image reading apparatus 11 includes a first moving mechanism 47 and a second moving mechanism 48. The first moving mechanism 47 is a moving mechanism for reciprocating the optical head 29 in the main scanning direction X. The first moving mechanism 47 is configured to include, for example, a rail for movably attaching the optical head 29 to the substrate 44 in the main scanning direction X, a motor or an actuator for generating driving force for moving the optical head 29, and a driving force transmission mechanism such as a belt or a gear for transmitting driving force.

The second moving mechanism 48 is a moving mechanism for moving the substrate 44 and the concave mirror 42 in the sub-scanning direction Y. By moving the substrate 44 in the sub-scanning direction Y, the optical head 29 attached to the substrate 44 moves in the sub-scanning direction Y. The second moving mechanism 48 is configured to include, for example, a motor or an actuator for generating driving force for moving the substrate 44 and the concave mirror 42 and a driving force transmission mechanism such as a belt or a gear for transmitting driving force. The first moving mechanism 47 and the second moving mechanism 48 drive the optical head 29 to move the optical head 29 in the main scanning direction X and the sub-scanning direction Y.

FIG. 5 shows the trajectory of the movement of the optical head 29 in reciprocating scanning. In scanning in the main scanning direction X, the optical head 29 moves in the right direction, for example, while scanning the first line indicated by L1. After scanning the line L1, the optical head 29 moves by one line in the sub-scanning direction Y, and moves in the left direction while scanning the next second line indicated by L2.

After scanning the line L2, the optical head 29 moves by one line in the sub-scanning direction Y to scan the third line indicated by L3. The movement direction while scanning the line L3 is a right direction. After scanning the line L3, the optical head 29 moves by one line in the sub-scanning direction Y to scan the fourth line indicated by L4. The movement direction while scanning the line L4 is a left direction.

Thus, the movement direction of the optical head 29 at the time of reading is reversed in odd-numbered lines, such as the line L1 and the line L3, and even-numbered lines, such as the line L2 and the line L4. Assuming that the scanning of one of the odd line and the even line is forward scanning, the scanning of the other line is backward scanning. The optical head 29 repeats the scanning in the main scanning direction X and the sub-scanning direction Y as described above, thereby performing scanning for reading a one-dimensional line image extending in the main scanning direction X line by line. The optical head 29 scans the entire surface of the image carrier 13 by performing scanning in the sub-scanning direction Y in combination with reciprocal scanning. In the event that the entire surface of the image carrier 13 is scanned, a two-dimensional image is read.

Figure 6:
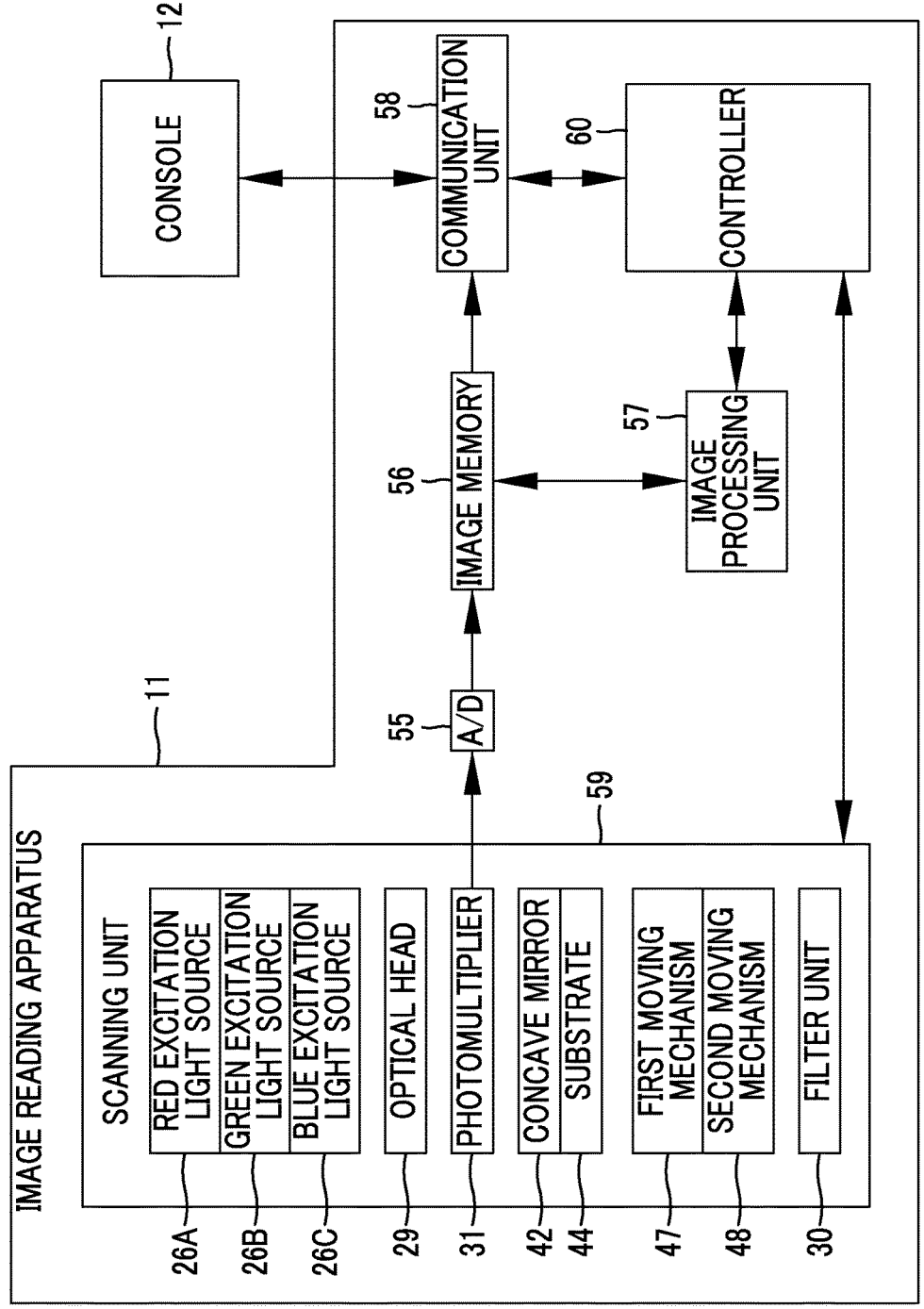
FIG. 6 is a block diagram of an image reading apparatus.

In FIG. 6, an analog/digital (A/D) converter (A/D) 55 is connected to the photomultiplier 31. The A/D 55 sequentially converts analog image signals, which are output sequentially from the photomultiplier 31 at predetermined timings, into digital image signals. The A/D 55 outputs each digital image signal to an image memory 56.

According to the forward scanning or backward scanning of the optical head 29, the light DL for one line is sequentially input to the photomultiplier 31. The photomultiplier 31 outputs an analog image signal of a line image corresponding to the light DL for one line that is sequentially input. The analog image signal for one line is converted into a digital image signal. Digital image signals of line images are sequentially recorded in the image memory 56. In the event that the optical head 29 scans the entire surface of the image carrier 13, a digital image signal (two-dimensional image) for one frame is recorded in the image memory 56.

An image processing unit 57 and a communication unit 58 are connected to the image memory 56. The image processing unit 57 performs various kinds of image processing on the image recorded in the image memory 56. The communication unit 58 is, for example, a USB communication interface, and is responsible for communication of various kinds of data with the console 12. The communication unit 58 receives an image after image processing from the image memory 56, and transmits the image to the console 12.

The excitation light sources 26A to 26C, the optical head 29, the photomultiplier 31, the concave mirror 42, the substrate 44, the first moving mechanism 47, the second moving mechanism 48, and the filter unit 30 form a scanning unit 59 that performs scanning for reading a two-dimensional image from the image carrier 13. The controller 60 performs overall control of the scanning unit 59, the image processing unit 57, the communication unit 58, and the like. The scanning unit 59 performs scanning under the control of the controller 60.

The console 12 is obtained by installing application software for realizing an operating system or an image display function with a personal computer or a workstation as its base. The image read by the image reading apparatus 11 is displayed on the console 12.

Figure 7:
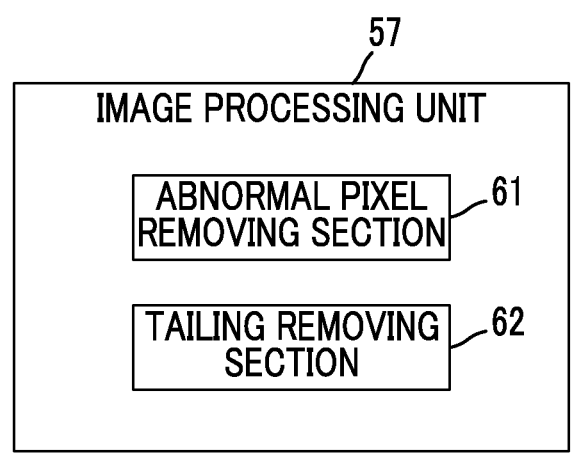
FIG. 7 is a block diagram of an image processing unit.

As shown in FIG. 7, the image processing unit 57 acquires a read image 65 from the scanning unit 59, and performs image processing on the read image 65. The image processing unit 57 includes an abnormal pixel removing section 61 and a tailing removing section 62 as an image correction section. For example, the image processing unit 57 may be realized by hardware, such as a digital signal processor (DSP) or field-programmable gate array (FPGA), or may be realized by a central processing unit (CPU) that executes image processing software. The image processing software is an operation program causing the CPU to realize a function as an image processing apparatus. The abnormal pixel removing section 61 removes a dot-shaped abnormal pixel, which is generated as a high-density significant point, in the read image. An abnormal pixel is generated, for example, due to dust. The tailing removing section 62 removes tailing occurring in the read image.

Hereinafter, the tailing removal processing and the abnormal pixel removal processing performed by the tailing removing section 62 and the abnormal pixel removing section 61 will be described.

(Tailing Removal Processing)

Figure 8:
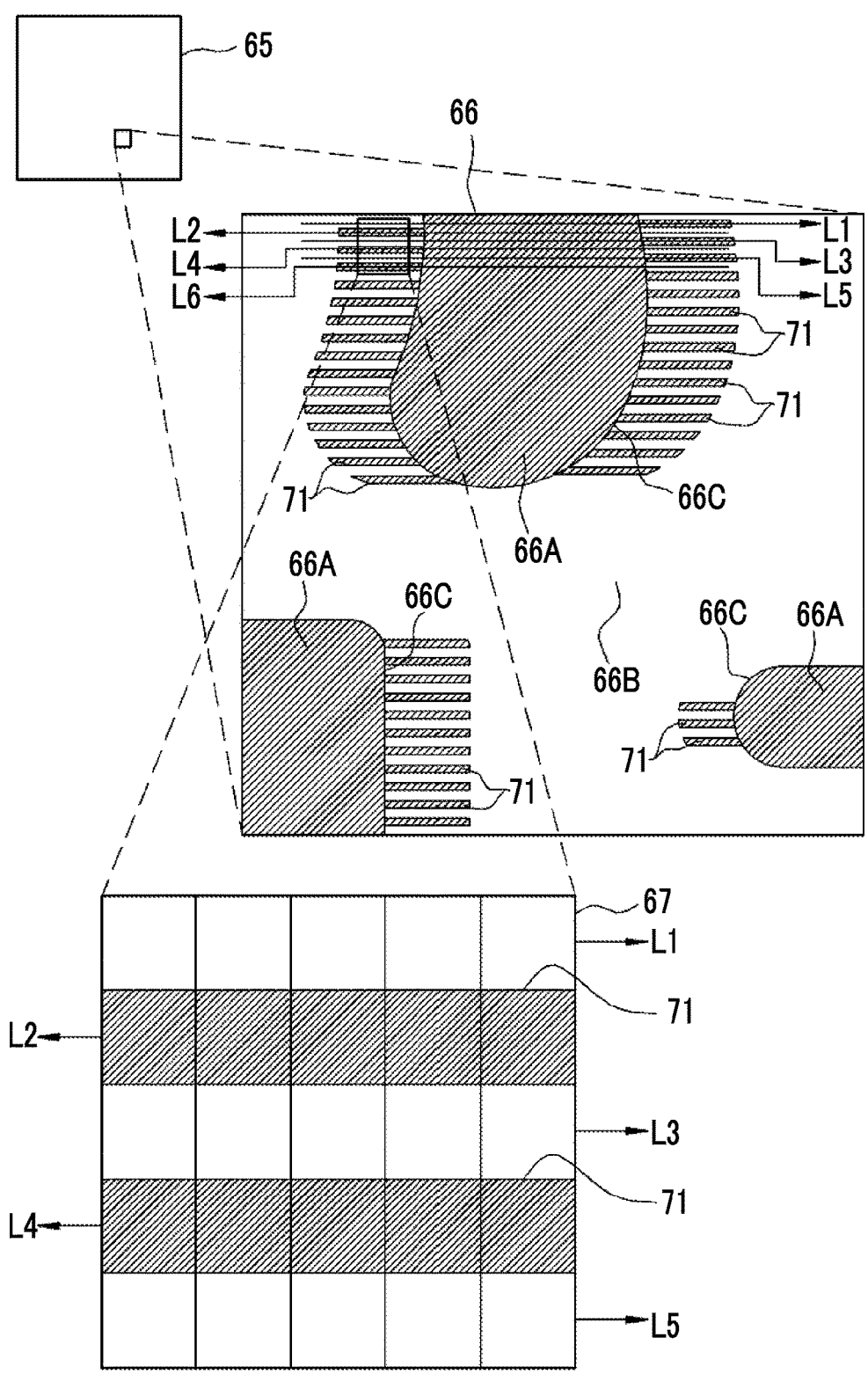
FIG. 8 is an explanatory diagram of a tailing image.

In FIG. 8 showing an image in which tailing has occurred, an image obtained by enlarging a part of the read two-dimensional image for one frame (hereinafter, referred to as a read image) 65 is a partial image 66. An image of a region where tailing has occurred in the partial image 66 is shown as a tailing image 67. For example, in a case where a high density region 66A is present in the partial image 66, a sharp density change occurs at the outline of the high density region 66A, that is, at a boundary 66C between the high density region 66A and a low density region 66B.

Tailing 71 occurs at the boundary 66C where such a sharp density change occurs. Assuming that the response speed of the photomultiplier 31 is lower than the scanning speed in the main scanning direction X, the photomultiplier 31 may not be able to follow the sharp density change. In a case where the optical head 29 moves from the high density region 66A to the low density region 66B, the optical head 29 moves from the high density region 66A to the low density region 66B across the boundary 66C. At this time, the output of the high density region 66A is also dragged in the low density region 66B. As a result, tailing of the high density region 66A occurs in the low density region 66B. It is known that the tailing 71 is more likely to occur as the applied voltage becomes lower to cause the response delay of the photomultiplier 31.

In the case of the reciprocating scanning method, since the scanning direction in the main scanning direction X changes every line, the direction in which the tailing 71 occurs changes every line. Therefore, in the reciprocating scanning method, at the boundary 66C of the high density region 66A, the tailing 71 occurs every other line, and the tailing 71 as a whole becomes a stripe shape extending in the main scanning direction X. The tailing image 67 is an enlarged image of a stripe-shaped tailing region.

The tailing image 67 shows a part of the tailing region generated in the partial image 66. In the tailing image 67, the tailing 71 occurs in the even-numbered lines L2 and L4, but does not occur in the odd-numbered lines L1, L3, and L5.

Figure 9:
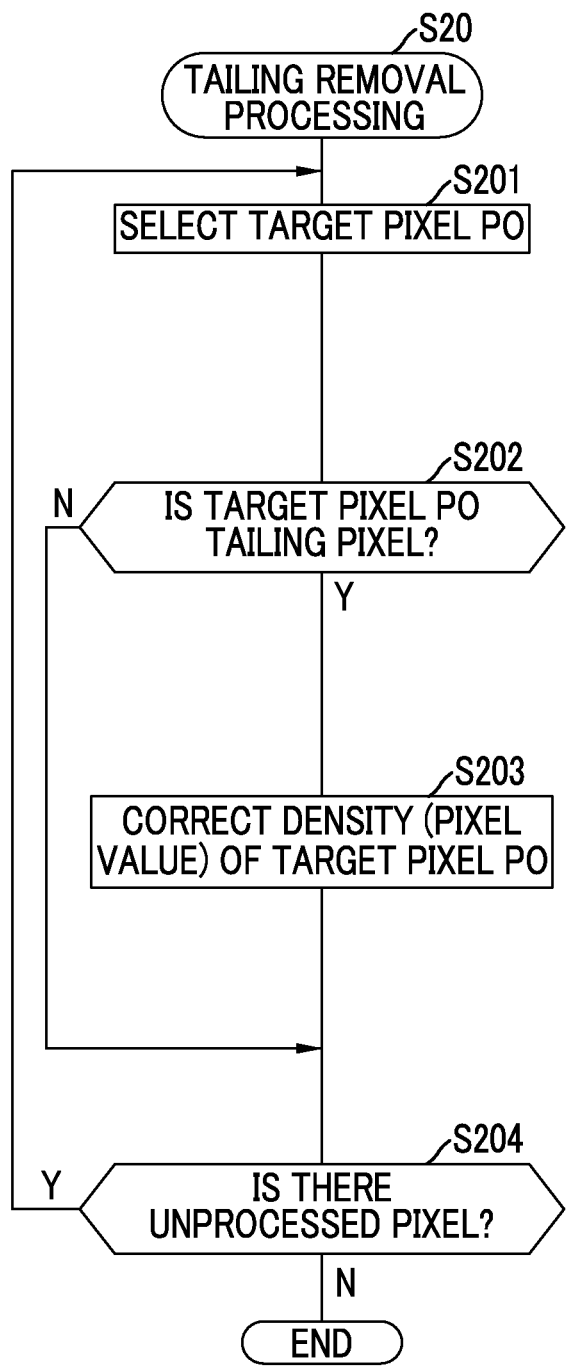
FIG. 9 is a flowchart showing the procedure of tailing removal processing.
Figure 10:
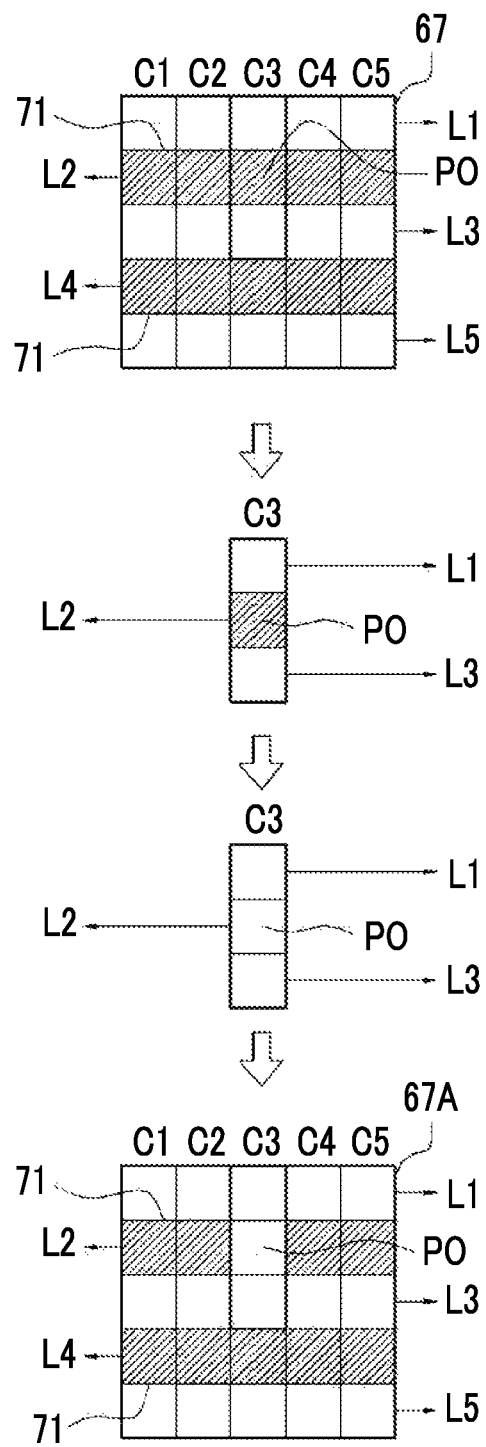
FIG. 10 is an image transition diagram showing the overview of tailing removal processing.

FIGS. 9 to 11 show tailing removal processing S20 performed by the tailing removing section 62. FIG. 9 is a flowchart showing the procedure of the tailing removal processing S20. FIG. 10 is an explanatory diagram of the processing contents of the tailing removal processing S20, and shows the image transition of the tailing image 67 according to the procedure of the tailing removal processing S20. The image transition in FIG. 10 corresponds to each of processing steps S201 to S203 in FIG. 9.

In FIG. 9, first, in the processing step S201, the tailing removing section 62 selects one pixel in the tailing image 67 as a target pixel PO to be corrected. In this example, as shown in FIG. 10, a pixel in a column C3 at the center of a line L2 is selected as the target pixel PO.

Then, in the processing step S202, the tailing removing section 62 determines whether or not the target pixel PO is a tailing pixel forming the tailing 71. Whether or not the target pixel PO is a tailing pixel is determined by comparing the density of the target pixel PO with the densities of pixels located above and below the target pixel PO (pixels of the lines L1 and L3 in the column C3), more specifically, comparing pixel values thereof indicating the densities with each other. In the reciprocating scanning, since tailing occurs every other line, the tailing 71 does not occur in upper and lower lines, which are adjacent to the line in which the tailing 71 occurs in the sub-scanning direction Y. Therefore, the difference in density between the line of the tailing 71 and the upper and lower lines adjacent to the line of the tailing 71 is large.

In the processing step S202, the tailing removing section 62 extracts three pixels of the target pixel PO and pixels, which are located above and below the target pixel PO, from the tailing image 67. In this example, as shown in FIG. 10, three pixels of the lines L1 to L3 in the column C3 are extracted. For example, in a case where the pixel value of the target pixel PO is higher than the pixel values of pixels located above and below the target pixel PO and the difference between the pixel value of the target pixel PO and the pixel values of the pixels located above and below the target pixel PO is equal to or greater than a predetermined value, tailing determination processing for determining that the target pixel PO is a tailing pixel is performed.

In a case where it is determined that the target pixel PO is a tailing pixel as a result of the tailing determination processing (Y in S202), the tailing removing section 62 proceeds to the processing step S203 to correct the pixel value of the target pixel PO. The correction method is, for example, a method of replacing the pixel value of the target pixel PO with the average value of the pixel values of the pixels located above and below the target pixel PO. Since the pixels located above and below the target pixel PO are not tailing pixels, the target pixel PO is replaced with a pixel value of a pixel that is not a tailing pixel. As a result, in FIG. 10, as shown in a tailing image 67A after the tailing removal processing on the target pixel PO, the tailing 71 is removed with respect to the target pixel PO of the line L2 in the column C3.

The tailing removing section 62 proceeds to processing step S204 to determine whether or not there is an unprocessed pixel. In a case where there is an unprocessed pixel, the processing steps S201 to 203 are repeated with the unprocessed pixel as a next target pixel PO. For example, in the line L2, pixels in the columns C1, C2, C4, and C5 are unprocessed pixels. Accordingly, the tailing removal processing S20 is performed on these pixels. As a result, in the tailing image 67, the tailing 71 of the line L2 is removed.

In this example, for the sake of convenience, an example has been described in which a pixel located in the column C3 located in the middle of the line L2 is selected as the target pixel PO ahead of the columns C1 and C2 located on the left side of the column C3 and the pixel is corrected. In practice, however, pixels are selected and corrected in order from the left to the right of the image, for example.

Assuming that such tailing removal processing S20 is also performed for the line L4, the entire tailing 71 of the tailing image 67 is removed. The tailing removing section 62 performs such tailing removal processing S20 on the entire read image 65 shown in FIG. 8. As a result, the tailing 71 in the read image 65 is removed.

FIG. 11 shows processing in a case where the selected target pixel PO is not a tailing pixel (N in processing step S202) in the tailing removal processing S20. The image transition in FIG. 11 corresponds to each of processing steps S201 to S203 in FIG. 9.

In the processing step S201, as shown in FIG. 11, for example, a pixel (which is not a tailing pixel) of the line L3 in the column C3 is selected as the target pixel PO. In this case, in the processing step S202, the tailing removing section 62 determines whether or not the target pixel PO is a tailing pixel. In this determination, the tailing removing section 62 compares the pixel value of the target pixel PO with the pixel values of pixels (pixels of the lines L2 and L4 in the column C3) located above and below the target pixel PO in the column C3. Since the target pixel PO is not a tailing pixel, the pixel value of the target pixel PO is lower than the pixel values of the pixels located above and below the target pixel PO. Since the pixel value of the target pixel PO is not higher than the pixel values of the pixels located above and below the target pixel PO by a predetermined value or more, the tailing removing section 62 determines that the target pixel PO is not a tailing pixel. In this case, the tailing removing section 62 skips the processing step S203, and proceeds to the processing step S204. That is, as shown in the processed tailing image 67A after the processing step S204, the density (pixel value) of the target pixel PO is not corrected.

As shown in FIG. 10, in a case where the target pixel PO is a tailing pixel, the tailing 71 is removed. As shown in FIG. 11, in a case where the target pixel PO is not a tailing pixel, correction is not performed. Therefore, regardless of whether or not the target pixel PO is a tailing pixel, the tailing removal processing is performed on all pixels of the read image 65, but appropriate correction is performed only for the tailing pixel. As a result, the tailing 71 is removed.

(Problems in a Case where an Abnormal Pixel is Present in a Tailing Region)

Figure 12:
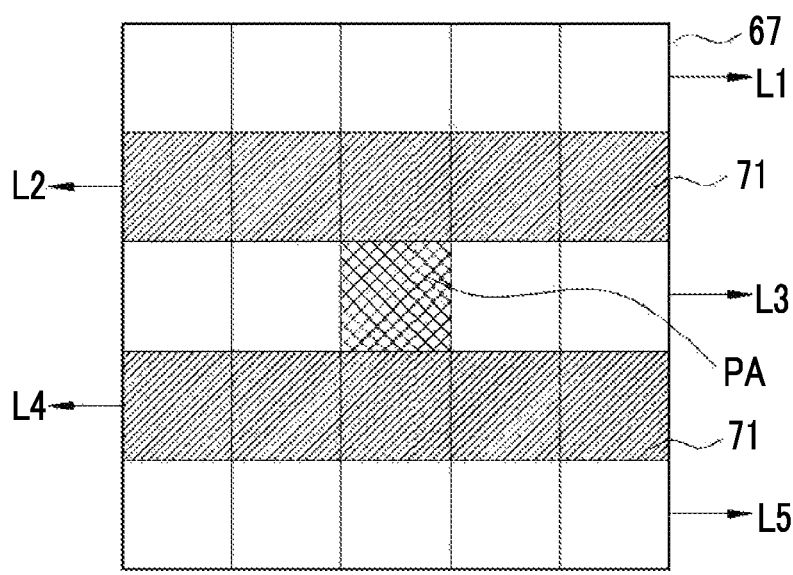
FIG. 12 is an explanatory diagram of a tailing image in which tailing and an abnormal pixel are mixed.

However, as shown in FIG. 12, in the tailing image 67, in the event that an abnormal pixel PA is present in a tailing region where the tailing 71 occurs, the tailing 71 may not be able to be appropriately removed even assuming that tailing removal processing is performed as shown in FIG. 13. FIG. 13 shows image transition in a case where the tailing removal processing is applied to the tailing image 67 shown in FIG. 12.

As shown in FIG. 13, the tailing removing section 62 performs the processing step S201 (refer to FIG. 9) to select one pixel (abnormal pixel PA of the line L2 in the column C3) in the tailing image 67 as the target pixel PO. As shown in FIG. 13, a case is considered in which the tailing removing section 62 selects a pixel in the column C3 at the center of the line L2 where the tailing 71 occurs in the tailing image 67, as the target pixel PO, in the same manner as in FIG. 10.

In the processing step 202, in the same manner as described in FIG. 10, the tailing removing section 62 compares the density (pixel value) of the target pixel PO with the densities (pixel values) of pixels located above and below the target pixel PO (pixels of the lines L1 and L3 in the column C3), and determines that the target pixel PO is a tailing pixel in a case where the pixel value of the target pixel PO is high and the difference between the pixel value of the target pixel PO and the pixel values of the pixels located above and below the target pixel PO is equal to or greater than a predetermined value. Here, the predetermined value is a value of 0 or more.

In FIG. 13, the pixel (pixel of the line L3 in the column C3) located below the target pixel PO is the abnormal pixel PA. Even in a case where the pixel value of the abnormal pixel PA is higher or lower than the pixel value of the target pixel PO that is a tailing pixel 71A, it can be considered that the difference between the pixel value of the abnormal pixel PA and the pixel value of the target pixel PO is less than the predetermined value. Therefore, the tailing removing section 62 erroneously determines that the target pixel PO is not the tailing pixel 71A even though the target pixel PO is the tailing pixel 71A (N in processing step S202). Then, the processing step S203 is skipped. As a result, the target pixel PO is not corrected and remains as the tailing pixel 71A.

Figure 14:
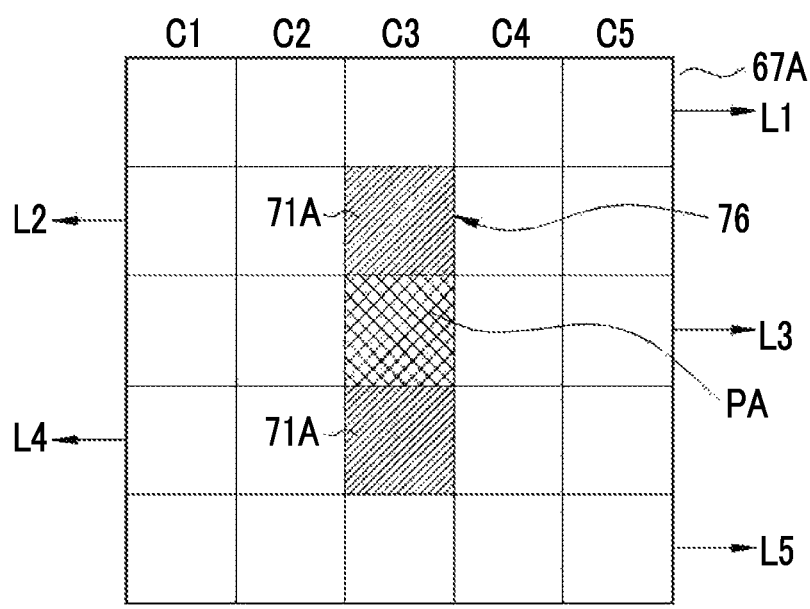
FIG. 14 is an explanatory diagram of a tailing image in which artifacts remain.

In the column C3, even in a case where the abnormal pixel PA of the line L3 or the tailing pixel of the line L4 below the line L3 is selected as the target pixel PO, appropriate correction is not performed since these pixels are not determined to be tailing pixels. Therefore, even in a case where the tailing removal processing is applied to all pixels in the tailing image 67, the tailing pixels 71A of the lines and L2 and L4 and the abnormal pixel PA of the line L3 are not appropriately corrected in the column C3 in the tailing image 67A after the tailing removal processing, as shown in FIG. 14. As a result, in the tailing image 67A, an artifact 76 in a form in which the three pixels are vertically arranged remains.

(Abnormal Pixel Removal Processing)

Figure 15:
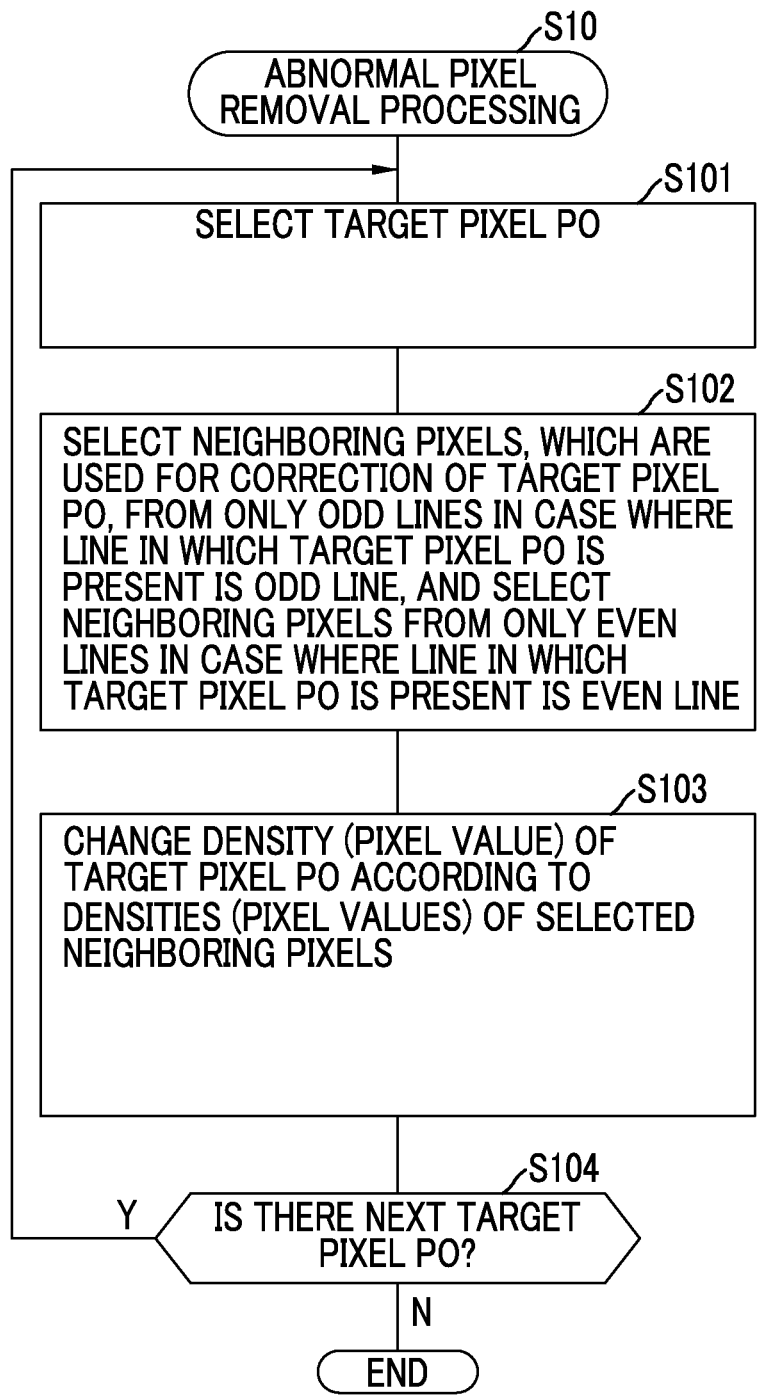
FIG. 15 is a flowchart showing the procedure of abnormal pixel removal processing.

Therefore, the abnormal pixel removing section 61 performs abnormal pixel removal processing S10 for appropriately removing the abnormal pixel PA generated in the tailing region, as shown in FIG. 15, so that the artifact 76 shown in FIG. 14 is not generated.

Figure 16:
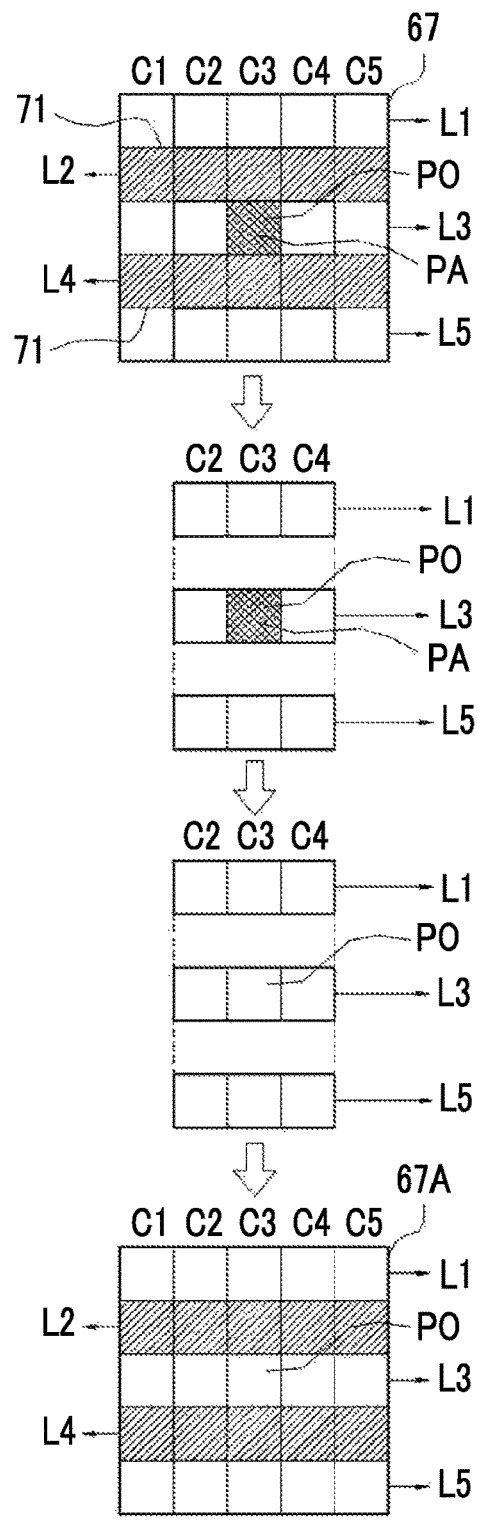
FIG. 16 is an image transition diagram showing the overview of abnormal pixel removal processing.

FIG. 15 is a flowchart showing the procedure of the abnormal pixel removal processing S10. FIG. 16 is an explanatory diagram of the processing contents of the abnormal pixel removal processing S10 performed on the tailing image 67 in which the abnormal pixel PA is present, and shows the image transition of the tailing image 67 according to the procedure of the abnormal pixel removal processing S10. The image transition in FIG. 16 corresponds to each of processing steps S101 to S103 in FIG. 15.

In FIG. 15, first, in the processing step S101, the abnormal pixel removing section 61 selects one pixel in the tailing image 67 as the target pixel PO that is to be corrected in order to remove an abnormal pixel. In this example, as shown in FIG. 16, the abnormal pixel PA in the column C3 at the center of the line L3 is selected as the target pixel PO. The line L3 is a line interposed between the lines L2 and L4 of two tailings 71 that are located above and below the line L3.

Then, in the processing step S102, the abnormal pixel removing section 61 performs processing for removing the abnormal pixel PA based on neighboring pixels present around the target pixel PO. As in this example, in a case where the abnormal pixel PA is selected as the target pixel PO, the abnormal pixel PA is removed based on the neighboring pixels present around the selected abnormal pixel PA.

In a case where the line in which the abnormal pixel PA selected as the target pixel PO is present is an odd-numbered line in the sub-scanning direction, the abnormal pixel removing section 61 selects neighboring pixels, which are used for correction for removing the abnormal pixel PA, from only a plurality of odd lines including the odd line in which the target pixel PO (corresponding to the abnormal pixel PA in FIG. 16) is present. On the other hand, in a case where the line in which the target pixel PO is present is an even-numbered line in the sub-scanning direction, the abnormal pixel removing section 61 selects neighboring pixels from only a plurality of even lines including the even line in which the target pixel PO is present. Based on the selected neighboring pixels, the abnormal pixel removing section 61 performs processing for removing the abnormal pixel.

In this example, since the target pixel PO is present in the line L3 that is an odd line, the abnormal pixel removing section 61 selects neighboring pixels to be used for correction from a plurality of odd lines including the line L3, specifically, from only a total of three lines of the line L3, the line L1 that is an odd line located above the line L3, and the line L5 that is an odd line located below the line L3.

Then, in the processing step S103, the abnormal pixel removing section 61 changes the density (pixel value) of the target pixel PO according to the densities (pixel values) of the selected neighboring pixels. Specifically, the abnormal pixel removing section 61 excludes two neighboring pixels of a pixel indicating the highest pixel value and a pixel indicating the lowest pixel value from eight neighboring pixels around the target pixel PO, and calculates the average value of the pixel values of the six remaining neighboring pixels. The abnormal pixel removing section 61 replaces the pixel value of the target pixel PO with the calculated average value. As a result, the density (pixel value) of the abnormal pixel PA selected as the target pixel PO is reduced, and the abnormal pixel PA is removed.

Such abnormal pixel removal processing is performed on all pixels of the read image 65. Accordingly, pixels other than the abnormal pixel PA are also selected as the target pixel PO.

Figure 17:
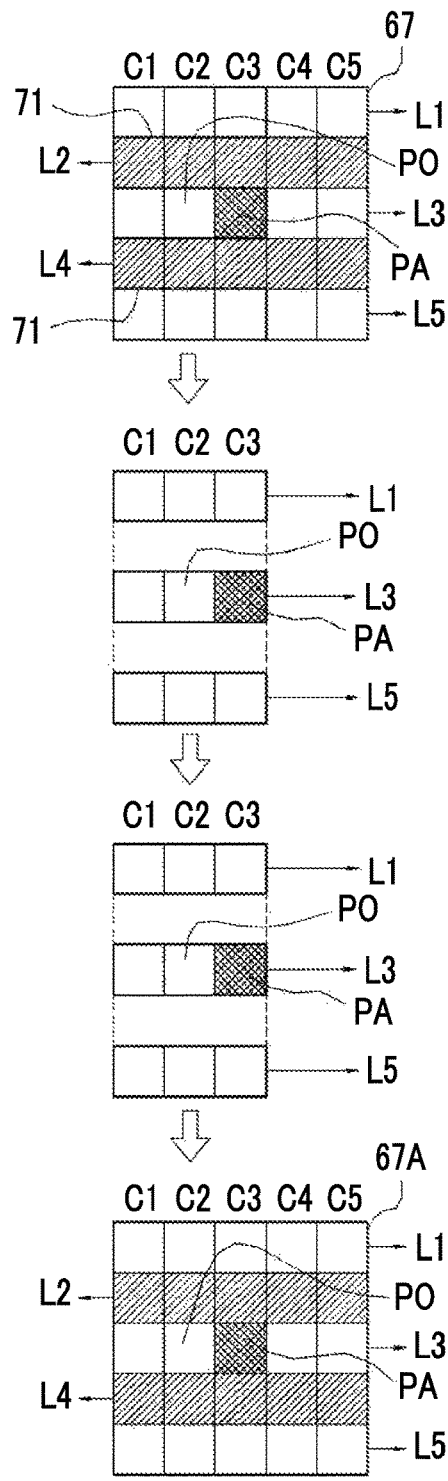
FIG. 17 is an explanatory diagram of abnormal pixel removal processing in a case where a pixel other than a tailing pixel and an abnormal pixel are selected as a target pixel.

FIG. 17 is an example in a case where a pixel selected as the target pixel PO is a pixel present in the line L3 between the lines L2 and L4 of the two tailings 71 as in the example shown in FIG. 16 but is not the abnormal pixel PA.

In the processing step S101, the abnormal pixel removing section 61 selects a pixel of the line L3 in the column C2 as the target pixel PO, as shown in FIG. 17.

Then, in the processing step S102, the abnormal pixel removing section 61 selects neighboring pixels from only odd lines since the target pixel PO is present in the line L3 that is an odd line. Specifically, eight neighboring pixels present around the target pixel PO are selected from two lines of the line L1, which is an odd line located above the line L3, and the line L5, which is an odd line located below the line L3.

In the processing step S103, the abnormal pixel removing section 61 excludes a pixel indicating the highest pixel value and a pixel indicating the lowest pixel value from the eight selected neighboring pixels, and calculates the average value of the pixel values of the six remaining neighboring pixels. The abnormal pixel PA is included in the eight selected neighboring pixels. However, the abnormal pixel PA is excluded from the average value calculation target since the abnormal pixel PA is a pixel having a highest pixel value among the eight neighboring pixels. Therefore, the pixel value of the abnormal pixel PA has no influence on the average value to be calculated.

Then, the pixel value of the target pixel PO is replaced with the calculated average value. In FIG. 17, since all neighboring pixels are selected from lines other than the line of the tailing 71, the pixel value of the target pixel PO is almost the same value as that before correction.

Figure 18:
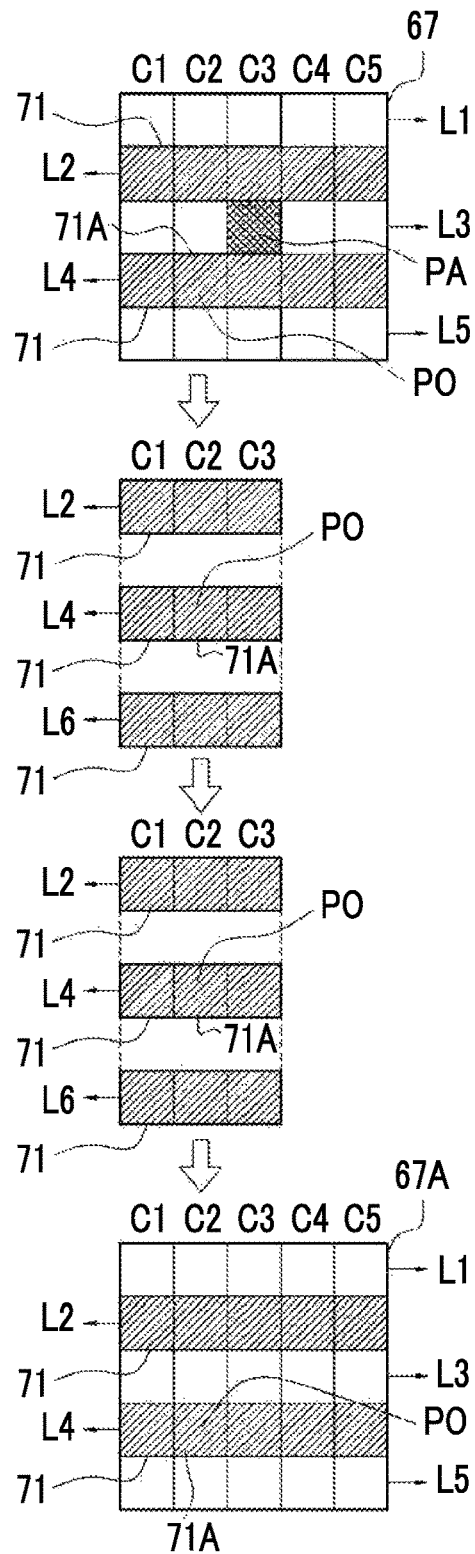
FIG. 18 is an explanatory diagram of abnormal pixel removal processing in a case where a tailing pixel is selected as a target pixel.

FIG. 18 shows an example in a case where a pixel selected as the target pixel PO is the tailing pixel 71A included in the line of the tailing 71. In the processing step S101, the abnormal pixel removing section 61 selects the tailing pixel 71A present in the line of the tailing 71 (pixel of the line L4 in the column C2) as the target pixel PO, as shown in FIG. 18.

Then, in the processing step S102, the abnormal pixel removing section 61 selects neighboring pixels from only even lines since the target pixel PO is present in the line L4 that is an even line. Specifically, eight neighboring pixels present around the target pixel PO are selected from two lines of the line L2, which is an even line located above the line L4, and the line L6, which is an even line located below the line L4.

In the processing step S103, the abnormal pixel removing section 61 excludes a pixel indicating the highest pixel value and a pixel indicating the lowest pixel value from the eight selected neighboring pixels, and calculates the average value of the pixel values of the six remaining neighboring pixels. Then, the pixel value of the target pixel PO is replaced with the calculated average value. In FIG. 18, since the target pixel PO is the tailing pixel 71A, all neighboring pixels are selected from the line of the tailing 71. Therefore, the pixel value of the tailing pixel 71A selected as the target pixel PO is almost the same value as that before correction. For this reason, even after the abnormal pixel removal processing S10 is performed, the tailing 71 remains as it is.

As shown by the tailing image 67, in the reciprocating scanning method, the tailing 71 occurs every other line in the sub-scanning direction Y. As shown in the processing step S102 (refer to FIG. 15), the abnormal pixel removing section 61 selects neighboring pixels from only odd lines or only even lines depending on whether the line in which the target pixel PO is an odd line or an even line.

Therefore, as shown in FIGS. 16 and 17, in a case where the target pixel PO is present between the two tailings 71, neighboring pixels are selected from lines other than the line of the tailing 71. As a result, the target pixel PO is appropriately corrected without being influenced by the tailing 71. Specifically, the abnormal pixel PA is removed in a case where the target pixel PO is the abnormal pixel PA as shown in FIG. 16, and the pixel value before correction is maintained in a case where the target pixel PO is not the abnormal pixel PA as shown in FIG. 17.

In addition, as shown in FIG. 18, in a case where the target pixel PO is the tailing pixel 71A, neighboring pixels are selected from only the line of the tailing 71. Therefore, since the target pixel PO is corrected according to the pixel values of the neighboring pixels selected from the tailing 71, the pixel value before correction is maintained.

Operation and Effect of the First Embodiment

Figure 19:
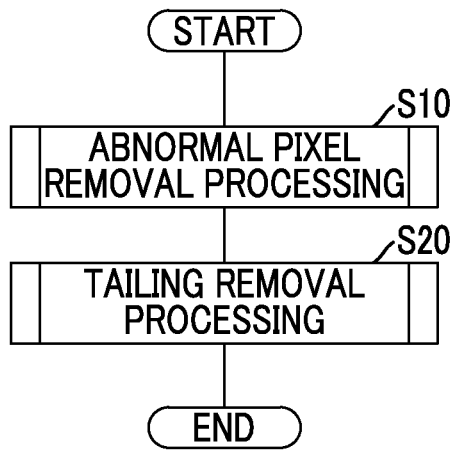
FIG. 19 is a flowchart showing the overall procedure of image processing of a first embodiment.

As shown in FIG. 19, first, the abnormal pixel removing section 61 of the image processing unit 57 performs the abnormal pixel removal processing S10 on all the pixels of the read image 65 that have been read by the scanning unit 59. In the abnormal pixel removal processing S10, as shown in the processing step S102, neighboring pixels to be used for correction are selected from only odd lines in a case where the line in which the target pixel PO is present is an odd line, and neighboring pixels to be used for correction are selected from only even lines in a case where the target pixel PO is present in an even line. Therefore, even in a case where the abnormal pixel PA is present in a tailing region where the tailing 71 occurring every other line is present due to the reciprocating scanning method, the abnormal pixel PA can be appropriately removed without being influenced by the tailing 71 as shown in FIG. 16.

After the abnormal pixel removal processing S10 is completed, the tailing removing section 62 performs the tailing removal processing S20. Since the abnormal pixel PA is removed by the abnormal pixel removal processing S10 before the tailing removal processing S20 is performed, an artifact shown in FIGS. 13 and 14 is not generated.

(Example of Processing for Selecting Only an Odd Line and an Even Line)

Figure 20:
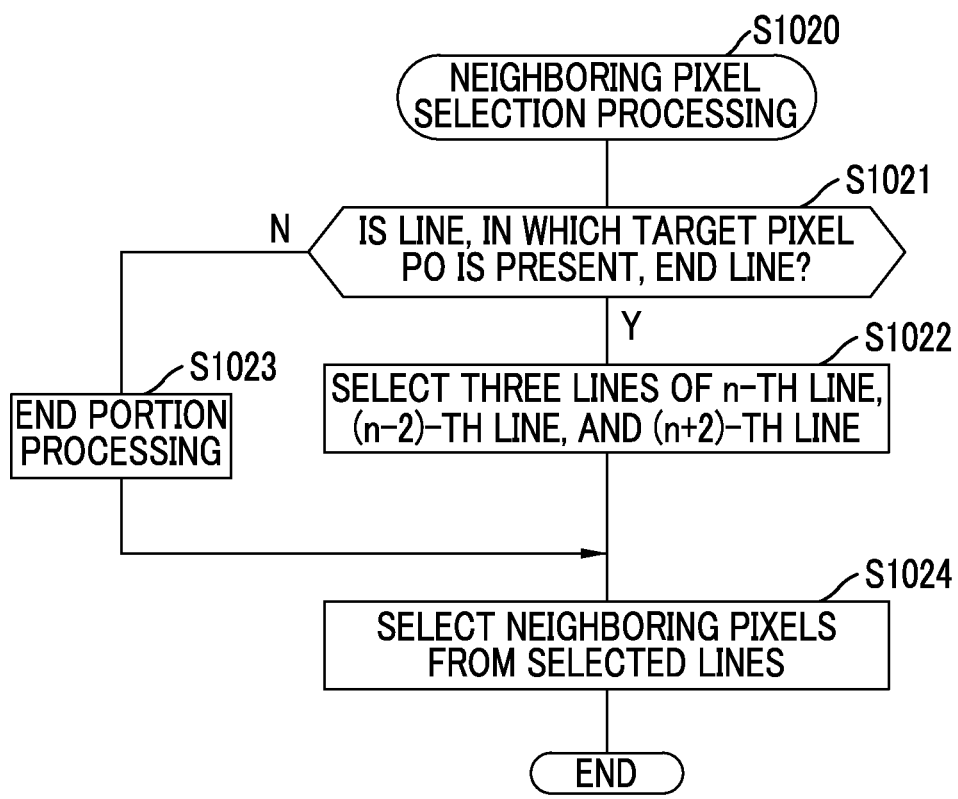
FIG. 20 is a flowchart showing an example of the procedure of neighboring pixel selection processing.

The flowchart of FIG. 20 shows an example of a method of selecting three lines as lines for selecting the neighboring pixels in the example described above. Neighboring pixel selection processing S1020 is a part of the processing step S102 shown in FIG. 15.

As shown in FIG. 20, in the neighboring pixel selection processing S1020, the abnormal pixel removing section 61 performs processing step S1021 first. In the processing step S1021, the abnormal pixel removing section 61 checks the line number n of the line, in which the target pixel PO is present, in the read image 65. Here, n is an integer of 1 or more. The line number n is "3" in the case of the third line, and the line number n is "6" in the case of the sixth line. Here, the line number in the read image 65 is given in order from the top of the read image 65.

After checking the line number n, the abnormal pixel removing section 61 determines whether or not the line in which the target pixel PO is present is an end line located in the upper end portion or the lower end portion in the read image 65. In this example, the end lines are two lines of the first and second lines L1 and L2 from the top, which are located in the upper end portion, and two lines of first and second lines from the end, which are located in the lower end portion. Assuming that the line number of the end line is "E", the first and second lines from the end are two lines of a line L(E) and a line L(E−1).

Determination regarding whether or not a line is an end line in processing step S1021 is performed according to, for example, the following Expression (1) in the case of selecting three lines including the line in which the target pixel PO is present as in this example. It is determined that the line is not an end line in a case where the line number n satisfies the conditions of the following Expression (1), and it is determined that the line is an end line in a case where the line number n does not satisfy the conditions of the following Expression (1).

$$3 \leq \text{line number } n \leq E-2 \quad (1)$$

The abnormal pixel removing section 61 proceeds to processing step S1022 in a case where the line in which the target pixel PO is present is not an end line, and proceeds to processing step S1023 in a case where the line in which the target pixel PO is present is an end line.

In processing step S1022, the abnormal pixel removing section 61 selects a total of three lines of an n-th line, an (n−2)-th line, and an (n+2)-th line. For example, in the case of n=3, the abnormal pixel removing section 61 selects a total of three lines of the third (3) line (line L3), the first (3−2) line (line L1), and the fifth (3+2) line (line L5). For example, in the case of n=4, the abnormal pixel removing section 61 selects a total of three lines of the fourth (4) line (line L4), the second (4-2) line (line L2), and the sixth (4+2) line (line L6). As a result, lines for selecting neighboring pixels are selected from only odd lines in a case where the line in which the target pixel PO is present is an odd line, and are selected from only even lines in a case where the line in which the target pixel PO is present is an even line.

In the end portion processing of the processing step S1023, the abnormal pixel removing section 61 sets a virtual line, which is not actually present, in the read image 65, as a neighboring pixel selection line. For example, in a case where the target pixel PO is present in the line L1 or the line L2 in the upper end portion, a line L0 and a line L(−1) are assumed. For example, the line L0 is generated by copying the value of the line L2 that is an even line located at a position symmetrical to the line L0 in the sub-scanning direction Y with the uppermost line L1 as a reference. The line L(−1) is generated by copying the value of the line L3 that is an odd line located at a position symmetrical to the line L(−1) in the sub-scanning direction Y with the uppermost line L1 as a reference.

In a case where a line L(−2) is assumed, the line L(−2) is generated by copying the value of the line L4 that is an even line located at a position symmetrical to the line L(−2) in the sub-scanning direction Y with the line L1 as a reference.

After assuming the line as described above, the abnormal pixel removing section 61 selects a total of three lines of an n-th line, an (n−2)-th line, and an (n+2)-th line. In a case where the target pixel PO is present in the line L1 (in the case of n=1), the abnormal pixel removing section 61 selects a total of three lines of the first (1) line (line L1), the (−1)-th (1−2) line (line L(−1)), and the third (1+2) line (line L3) as lines for selecting neighboring pixels. In a case where the target pixel PO is present in the line L2 (in the case of n=2), the abnormal pixel removing section 61 selects a total of three lines of the second (2) line (line L2), the (0)-th (2−2) line (line L0), and the fourth (2+2) line (line L4) as lines for selecting neighboring pixels.

Also in a case where the lines E and E−1 in the lower end portion are selected, a virtual line is similarly set and is used as a line for selecting neighboring pixels. The abnormal pixel removing section 61 selects lines in processing step S1022 or S1023, and then selects neighboring pixels from the selected lines in processing step S1024.

As described above, in a case where the line in which the target pixel PO is present is an end line located in the upper end portion or the lower end portion of the read image 65 in the sub-scanning direction, the abnormal pixel removing section 61 performs end portion processing in which a virtual line is additionally set at the upper end or the lower end of the read image 65 and the virtual line is used as the line for selecting the neighboring pixels. By performing the end portion processing, processing can also be performed in the end portion of the read image 65 without changing the basic logic of abnormal pixel removal processing.

Here, the upper end portion and the lower end portion are ranges from several lines to several tens of lines from the upper end and the lower end of the read image 65. Neighboring pixels are pixels in the range of several pixels to several tens of pixels around the target pixel PO as a reference.

The example shown in FIG. 20 is one example. Since various kinds of specific processing for selecting neighboring pixels from only odd lines or only even lines can be considered, any of the processes may be used.

In the above example, an example has been described in which a total of three lines are selected as lines for selecting neighboring pixels. However, five or more lines may be selected and neighboring pixels may be selected from the five lines or more. In the case of selecting five or more lines, 24 surrounding pixels excluding the target pixel PO are selected as neighboring pixels from 25 (5×5) pixels including the target pixel PO at the center.

Instead of a plurality of lines for selecting neighboring pixels, only one line in which the target pixel PO is present may be used. In this case, in a case where the line in which the target pixel PO is present is an odd line, the one odd line is a line for selecting neighboring pixels. In a case where the line in which the target pixel PO is present is an even line, the one even line is a line for selecting neighboring pixels. In a case where one line in which the target pixel PO is present is a line for selecting neighboring pixels, one or more pixels located on the left and right sides of the target pixel PO in each line are selected as neighboring pixels, for example.

For example, even in the case of selecting a total of three lines for selecting neighboring pixels, a total of three lines of an n-th line, an (n−4)-th line, and an (n+4)-th line may be selected instead of selecting a total of three lines of an n-th line, an (n−2)-th line, and an (n+2)-th line. In short, lines for selecting neighboring pixels may be selected from only either odd lines or even lines depending on whether the target pixel PO is an odd line or an even line.

(Method of Performing Tailing Determination Processing in a Plurality of Columns)

Figure 21:
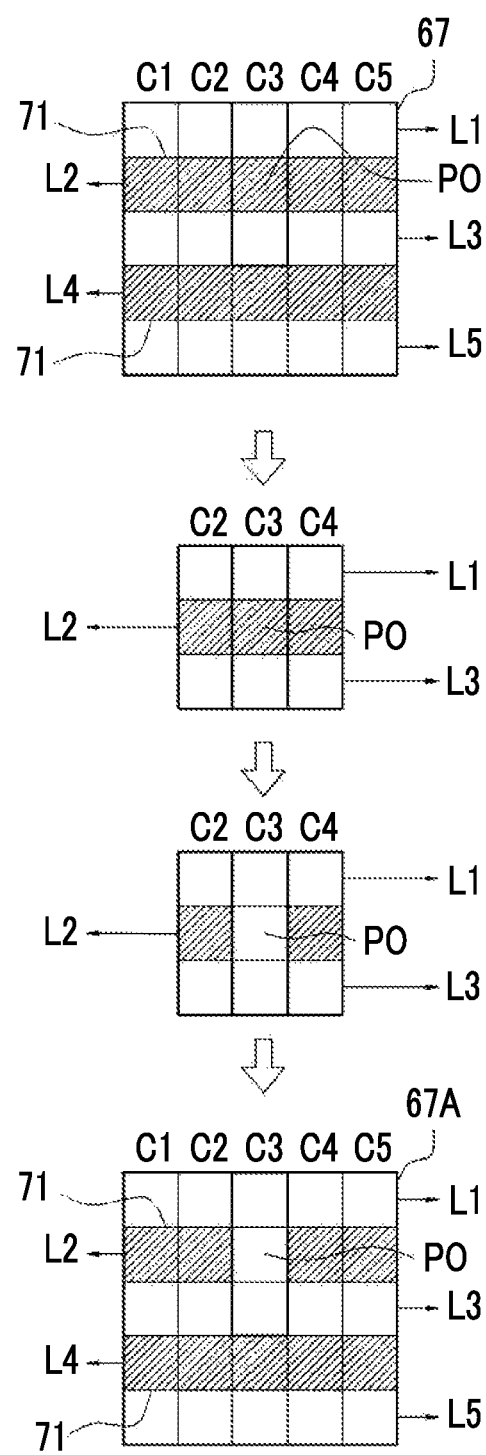
FIG. 21 is a flowchart showing the procedure of tailing removal processing.

In the above example, the tailing removing section 62 performs the tailing determination processing of processing step S202 in FIG. 9 by comparing the pixel value of the target pixel PO with the pixel values of pixels, which are located above and below the target pixel PO so as to be adjacent to the target pixel PO in the sub-scanning direction, in one column in which the target pixel PO is present, as shown in FIG. 10. As shown in FIG. 21, the tailing determination processing may be performed by using a plurality of columns including a column, which extends in the sub-scanning direction and in which the target pixel PO is present, and left and right columns thereof.

In FIG. 21, in the tailing determination processing, also for a plurality of columns including the column C3 in which the target pixel PO is present and the left and right columns C2 and C4 adjacent to the target pixel PO in the main scanning direction X, the tailing removing section 62 compares pixel values between upper and lower pixels adjacent to each other in the sub-scanning direction Y, and uses the comparison result in the tailing determination processing.

The tailing 71 extends in the main scanning direction X. Therefore, by using the result of comparison between the column C3 in which the target pixel PO is present and the left and right columns adjacent to the target pixel PO in the main scanning direction X, the accuracy of determination regarding whether or not the target pixel PO is a tailing pixel is improved.

Specifically, in the columns C2 and C4, the tailing removing section 62 compares the pixel value of a pixel in the line L2 in which the target pixel PO is present with the pixel value of each pixel in the lines L1 and L3 located above and below the line L2, thereby determining whether or not the pixel value of the pixel in the line L2 is higher than the pixel value of each pixel in the lines L1 and L3 and whether or not the difference between the pixel value of the pixel in the line L2 and the pixel value of each pixel in the lines L1 and L3 is equal to or greater than a predetermined value. For the columns C2 and C4, as in the case of the column C3, in a case where the pixel value of the pixel in the line L2 is higher than the pixel values of pixels located above and below the pixel in the line L2, the tailing removing section 62 determines that the target pixel PO is a tailing pixel.

Second Embodiment

Figure 22:
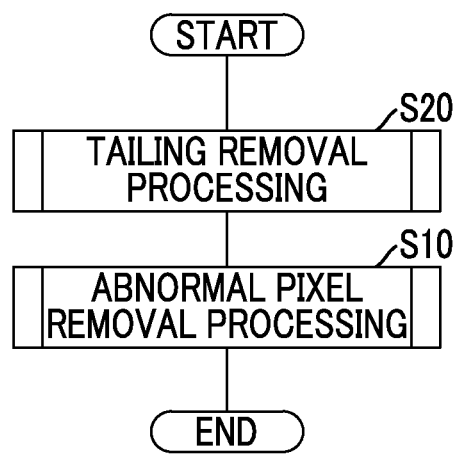
FIG. 22 is a flowchart showing the overall procedure of image processing of a second embodiment.
Figure 23:
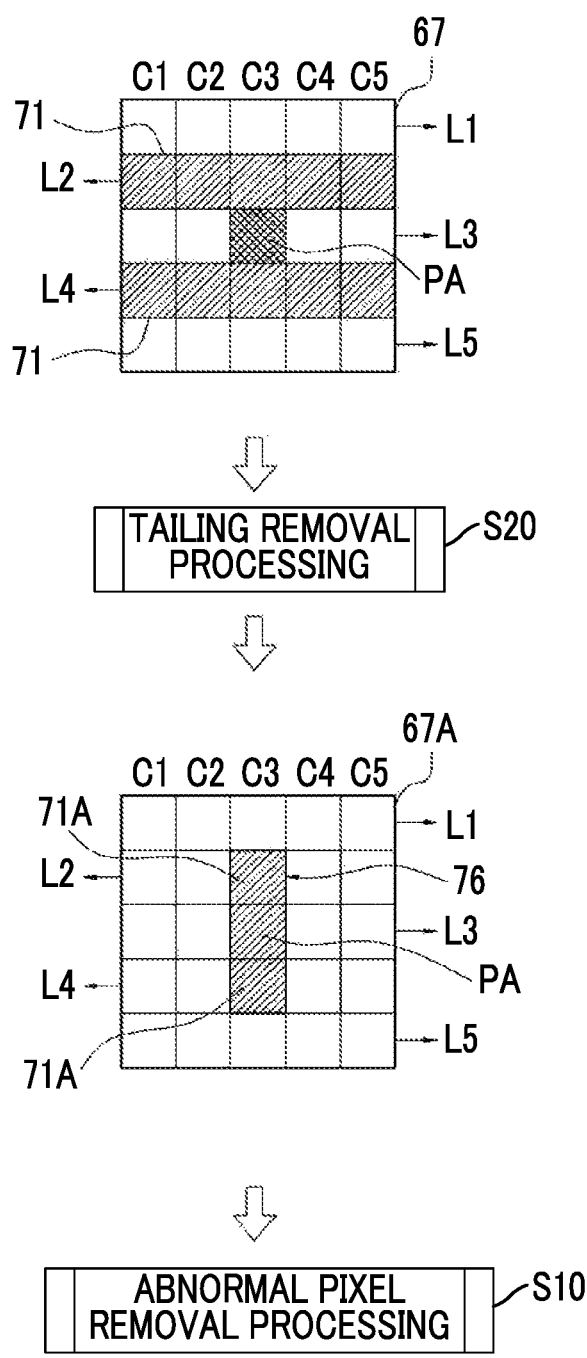
FIG. 23 is an image transition diagram showing the overview of the processing of the second embodiment.

FIGS. 22 and 23 show a second embodiment. In the first embodiment, as shown in FIG. 19, the tailing removal processing S20 is performed after performing the abnormal pixel removal processing S10. However, as in the second embodiment shown in FIG. 22, the abnormal pixel removal processing S10 may be performed after performing the tailing removal processing S20.

In the second embodiment, as shown in FIG. 23, the tailing removal processing S20 is performed on the tailing image 67 in which the abnormal pixel PA and the tailing 71 are mixed. In the example shown in FIG. 9, in a case where the pixel value of the target pixel PO is higher than the pixel values of pixels located above and below the target pixel PO and the difference between the pixel value of the target pixel PO and the pixel values of the pixels located above and below the target pixel PO is equal to or greater than a predetermined value, it is determined that the target pixel PO is a tailing pixel. In a case where it is determined that the target pixel PO is a tailing pixel, the pixel value of the target pixel PO is replaced with the pixel value of each pixel located above and below the target pixel PO so that tailing is removed. The tailing removing section 62 sequentially selects each pixel of the tailing image 67 shown in FIG. 23 as the target pixel PO, and performs the tailing removal processing S20.

However, in a case where the tailing removal processing S20 is performed on the tailing image 67 in which the abnormal pixel PA has not been removed, an artifact remains in the column C3 in which the abnormal pixel PA is present, as shown in the tailing image 67A after processing. This is because, in a case where the abnormal pixel PA is selected as the target pixel PO, the pixel value is the same as the pixel values of the tailing pixels 71A located above and below the abnormal pixel PA, and accordingly, tailing removal is not performed on the target pixel PO. Also in a case where the abnormal pixel PA and the tailing pixels 71A located above and below the abnormal pixel PA are selected as the target pixel PO, tailing removal is not performed similarly since the abnormal pixel PA is located between the upper and lower pixels.

The abnormal pixel removal processing S10 is performed on the tailing image 67A in which the artifact 76 remains. In this case, in addition to the abnormal pixel removal processing S10, processing for appropriately removing the artifact 76 is required. As the processing for removing the artifact 76, for example, it is conceivable to repeat the abnormal pixel removal processing S10. As described above, in the abnormal pixel removal processing S10, lines for selecting neighboring pixels are selected from only odd lines or even lines. Therefore, in a case where one of pixels forming the artifact 76 is selected as the target pixel PO, vertically adjacent pixels are excluded from neighboring pixels. Therefore, as neighboring pixels, many pixels other than the artifact 76 are included, so that the artifact 76 can be easily removed. However, as described above, in the second embodiment, additional processing is required as compared with the first embodiment. Therefore, it is preferable to perform the tailing removal processing after performing the abnormal pixel removal processing S10 as in the first embodiment.

In the above embodiment, an example of the tailing determination processing has been described in which the target pixel is determined to be a tailing pixel forming the tailing in a case where the pixel value of the target pixel PO is higher than the pixel values of pixels located above and below the target pixel PO and the difference between the pixel value of the target pixel PO and the pixel values of the pixels located above and below the target pixel PO is equal to or greater than a predetermined value. However, instead of using the difference between the pixel value of the target pixel PO and the pixel values of the pixels located above and below the target pixel PO, the determination may be performed using the ratio of pixel values. For example, assuming that the pixel value of the target pixel PO is VO and the pixel values of pixels located above and below the target pixel PO are VN, in a case where VO/VN that is a ratio between the pixel value of the target pixel PO and the pixel value of each of the pixels located above and below the target pixel PO is equal to or greater than a predetermined value, the target pixel PO may be determined to be a tailing pixel.

In the above embodiment, an example has been described in which the optical head 29 and the photomultiplier 31 are formed separately from each other. However, the photomultiplier 31 may be built into the optical head 29. In this case, in the event that the optical head 29 performs reciprocating scanning, the photomultiplier 31 itself also reciprocates.

Although the photomultiplier 31 has been described as an example of the optical sensor, other optical sensors that perform photoelectric conversion may be used without being limited to the photomultiplier 31. As other optical sensors, for example, there is an optical sensor using a photodiode. Also in the case of using a photodiode, the invention is effective since there is a possibility that the tailing 71 will occur due to a reduction in the response speed.

In the embodiment described above, for the relative movement between the optical head 29 and the image carrier 13 in the sub-scanning direction Y, the movement of the image carrier 13 in the sub-scanning direction Y is stopped while scanning one line in the main scanning direction X, and scanning is performed for one line in the main scanning direction X in the stopped state. Then, after completion of the scanning in the main scanning direction X for one line, the image carrier 13 is moved by one line in the sub-scanning direction Y to perform scanning in the main scanning direction X for the next line. In this manner, the relative movement in the sub-scanning direction Y is performed step by step.

The relative movement in the sub-scanning direction Y may be continuous feed for continuous movement instead of step by step. In this case, the optical head 29 moves in the main scanning direction X while the image carrier 13 is moving in the sub-scanning direction Y without being stopped. In the read image 65, each line along the main scanning direction X is slightly inclined, but it is possible to solve this problem by image correction.

The image carrier 13 and the optical head 29 may move relative to each other. In addition, although the image carrier 13 is moved in the sub-scanning direction Y, the optical head 29 may be moved in a state in which the image carrier 13 is stopped.

In the above embodiment, the form of the image processing apparatus of the invention has been described in which the image processing unit 57 is configured to include the abnormal pixel removing section 61 that performs the abnormal pixel removal processing S10 and the tailing removing section 62 that performs the tailing removal processing S20 and the image processing unit 57 is built into the image reading apparatus 11. The image processing apparatus may be configured separately from the image reading apparatus 11. The image processing unit 57 may be built into the console 12, and the console 12 may be used as the image processing apparatus.

Figure 24:
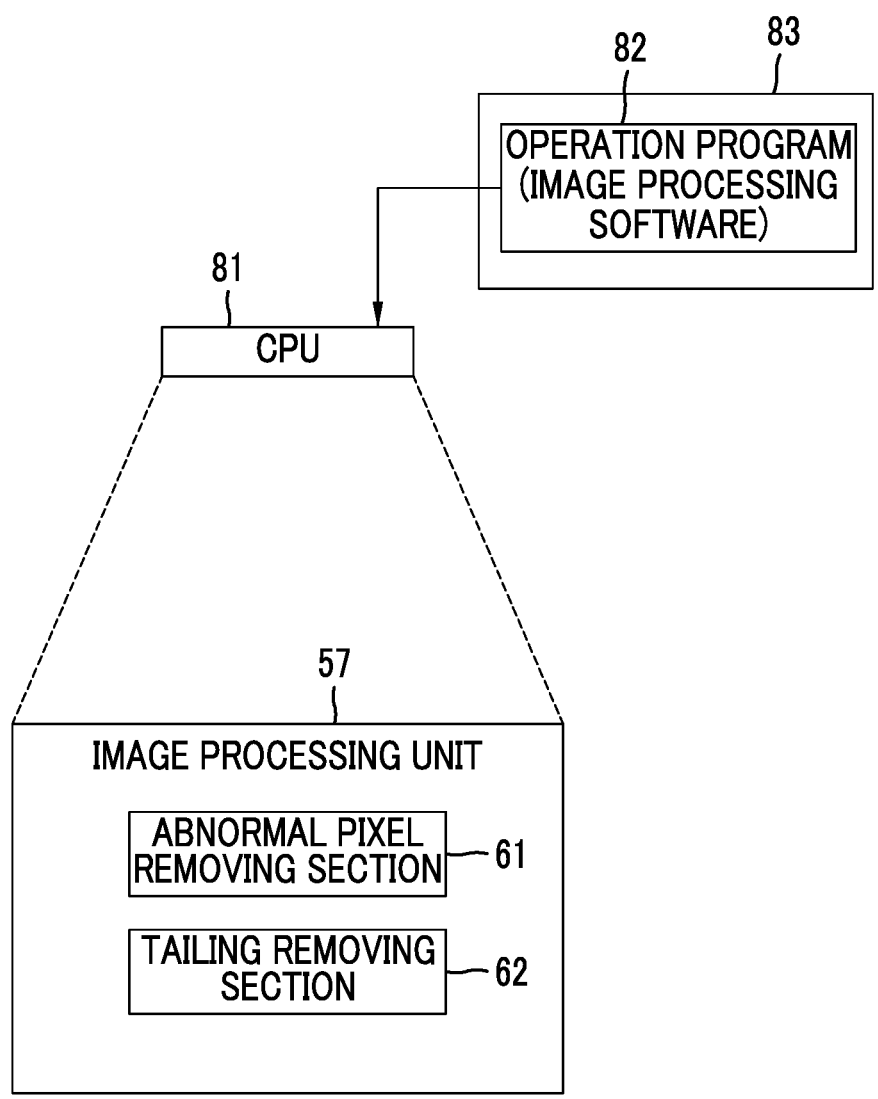
FIG. 24 is an explanatory diagram of an operation program.

As described above, the image processing apparatus of the invention may be configured by hardware, or may be realized by an operation program. For example, as shown in FIG. 24, an operation program 82 is image processing software, and a CPU 81 provided in the image reading apparatus 11 or the like performs the operation program 82 so that the CPU 81 functions as the image processing unit 57. Thus, the invention extends not only to the image processing apparatus but also to an image processing method executed by the image processing apparatus and an operation program of the image processing apparatus. In addition to the operation program, the invention also extends to a non-transitory storage medium 83 that stores the operation program.

In the above embodiment, an example using the image carrier 13 in which a biological substance is labeled with a fluorescent dye has been described. However, a stimulable phosphor sheet in which a radiographic image, an autoradiographic image, a radiation diffraction image, an electron microscopic image, and the like are recorded on a stimulable phosphor layer may be used. In this case, light to be detected is photostimulated light emitted from the stimulable phosphor.

In the invention, it is also possible to appropriately combine the above-described various embodiments or various modification examples. Without being limited to the embodiments described above, it is needless to say that various configurations can be adopted without departing from the scope of the invention.

EXPLANATION OF REFERENCES

10: image detection system
11: image reading apparatus
12: console
13: image carrier
14: housing
15, 16: lid
17: display
18: operation unit
25: stage
26A: excitation light source (red excitation light source)

26B: excitation light source (green excitation light source)
26C: excitation light source (blue excitation light source)
27: light source optical system
28: light guiding optical system
29: optical head
30: filter unit
31: photomultiplier
32: glass plate
33 to 35: collimator lens
36, 39, 40: mirror
37, 38: dichroic mirror
41: holed concave mirror
42, 50: concave mirror
43: through hole
44: substrate
45A: filter (red filter)
45B: filter (green filter)
45C: filter (blue filter)
45D: filter
47: first moving mechanism
48: second moving mechanism
51: aspheric lens
55: A/D converter (A/D)
56: image memory
57: image processing unit
58: communication unit
59: scanning unit
60: controller
61: abnormal pixel removing section
62: tailing removing section
65: read image (two-dimensional image)
66: partial image
66A: high density region
66B: low density region
66C: boundary
67, 67A: tailing image
71: tailing
71A: tailing pixel
76: artifact
81: CPU
82: operation program
83: storage medium
L1 to L6: line
C1 to C5: column
PO: target pixel
PA: abnormal pixel

What is claimed is:

1. An image processing apparatus connected to a scanning unit that performs scanning for image reading on an image carrier carrying image information by moving an optical head relative to the image carrier and that reads a one-dimensional line image in a main scanning direction line by line by performing reciprocating scanning, in which forward scanning and backward scanning are alternately repeated for each line in the main scanning direction, and reads a two-dimensional image by performing scanning in a sub-scanning direction perpendicular to the main scanning direction in combination with the reciprocating scanning, acquires the two-dimensional image from the scanning unit, and performs image processing on the two-dimensional image, the apparatus comprising:
a processor configured to:
remove an abnormal pixel present in the two-dimensional image by changing a pixel value thereof according to pixel values of neighboring pixels present around the abnormal pixel;
select the neighboring pixels from at least one odd line including an odd line, in which a target pixel for removing the abnormal pixel is present, in a case where the target pixel is present in an odd line in the sub-scanning direction;
select the neighboring pixels from at least one even line including an even line, in which the target pixel is present, in a case where the target pixel is present in an even line in the sub-scanning direction; and
remove stripe-shaped tailing from the two-dimensional image, the stripe-shaped tailing occurring every other line due to the reciprocating scanning in the two-dimensional image and extending in the main scanning direction,
wherein, in the removing stripe-shaped tailing, the processor performs tailing determination processing in which a pixel value of the target pixel is compared with pixel values of upper and lower pixels adjacent to the target pixel in the sub-scanning direction, and the target pixel is determined to be a tailing pixel forming the tailing in a case where the pixel value of the target pixel is higher than the pixel values of the upper and lower pixels and a difference or a ratio between the pixel value of the target pixel and the pixel values of the upper and lower pixels is equal to or greater than a predetermined value.

2. The image processing apparatus according to claim 1, wherein tailing removal processing for removing the tailing is performed after performing abnormal pixel removal processing for removing the abnormal pixel.

3. The image processing apparatus according to claim 1, wherein, in the abnormal pixel removal processing for removing the abnormal pixel, the number of lines for selecting the neighboring pixels is two or more.

4. The image processing apparatus according to claim 3, wherein, in the abnormal pixel removal processing, the lines for selecting the neighboring pixels include at least an n-th line, an (n−2)-th line, and an (n+2)-th line in a case where the line in which the target pixel is present is the n-th line (where n is an integer of 1 or more).

5. The image processing apparatus according to claim 4, wherein, in the abnormal pixel removal processing, in a case where the line in which the target pixel is present is an end line located in an upper end portion or a lower end portion of the two-dimensional image in the sub-scanning direction, the processor performs end portion processing in which a virtual line is additionally set at an upper end or a lower end of the two-dimensional image and the virtual line is used as the line for selecting the neighboring pixels.

6. The image processing apparatus according to claim 1, wherein the processor performs tailing determination processing in which a pixel value of the target pixel is compared with pixel values of upper and lower pixels adjacent to the target pixel in the sub-scanning direction and the target pixel is determined to be a tailing pixel forming the tailing in a case where the pixel value of the target pixel is higher than the pixel values of the upper and lower pixels and a difference or a ratio between the pixel value of the target pixel and the pixel values of the upper and lower pixels is equal to or greater than a predetermined value.

7. The image processing apparatus according to claim 6, wherein, in the tailing determination processing, for a plurality of columns including a column, which extends in the sub-scanning direction and in which the target pixel is present, and left and right columns adjacent to the target pixel in the main scanning direction, the processor compares pixel values between pixels adjacent to each other in the sub-scanning direction and uses a result of the comparison for tailing determination.

8. The image processing apparatus according to claim 1, wherein the image carrier contains a sample that emits fluorescence, and
the scanning unit has an excitation light source that generates excitation light to be emitted to the image carrier and an optical sensor that photoelectrically converts fluorescence that is excited by the excitation light and is received by the optical head.

9. An image processing method in which a scanning unit, which performs scanning for image reading on an image carrier carrying image information by moving an optical head relative to the image carrier and which reads a one-dimensional line image in a main scanning direction line by line by performing reciprocating scanning, in which forward scanning and backward scanning are alternately repeated for each line in the main scanning direction, and reads a two-dimensional image by performing scanning in a sub-scanning direction perpendicular to the main scanning direction in combination with the reciprocating scanning, is used, the two-dimensional image is acquired from the scanning unit, and image processing is performed on the two-dimensional image, the method comprising:
removing an abnormal pixel present in the two-dimensional image by changing a pixel value thereof according to pixel values of neighboring pixels present around the abnormal pixel;
selecting the neighboring pixels from at least one odd line including an odd line, in which a target pixel for removing the abnormal pixel is present, in a case where the target pixel is present in an odd line in the sub-scanning direction;
selecting the neighboring pixels from at least one even line including an even line, in which the target pixel is present, in a case where the target pixel is present in an even line in the sub-scanning direction; and
removing stripe-shaped tailing from the two-dimensional image, the stripe-shaped tailing occurring every other line due to the reciprocating scanning in the two-dimensional image and extending in the main scanning direction,
wherein, in the removing stripe-shaped tailing, tailing determination processing is performed in which a pixel value of the target pixel is compared with pixel values of upper and lower pixels adjacent to the target pixel in the sub-scanning direction, and the target pixel is determined to be a tailing pixel forming the tailing in a case where the pixel value of the target pixel is higher than the pixel values of the upper and lower pixels and a difference or a ratio between the pixel value of the target pixel and the pixel values of the upper and lower pixels is equal to or greater than a predetermined value.

10. A non-transitory computer readable medium for storing a computer-executable program for execution of image processing that uses a scanning unit that performs scanning for image reading on an image carrier carrying image information by moving an optical head relative to the image carrier and that reads a one-dimensional line image in a main scanning direction line by line by performing reciprocating scanning, in which forward scanning and backward scanning are alternately repeated for each line in the main scanning direction, and reads a two-dimensional image by performing scanning in a sub-scanning direction perpendicular to the main scanning direction in combination with the reciprocating scanning, acquires the two-dimensional image from the scanning unit, and performs image processing on the two-dimensional image,
wherein the computer-executable program includes:
removing an abnormal pixel present in the two-dimensional image by changing a pixel value thereof according to pixel values of neighboring pixels present around the abnormal pixel;
selecting the neighboring pixels from at least one odd line including an odd line, in which a target pixel for removing the abnormal pixel is present, in a case where the target pixel is present in an odd line in the sub-scanning direction;
selecting the neighboring pixels from at least one even line including an even line, in which the target pixel is present, in a case where the target pixel is present in an even line in the sub-scanning direction; and
removing stripe-shaped tailing from the two-dimensional image, the stripe-shaped tailing occurring every other line due to the reciprocating scanning in the two-dimensional image and extending in the main scanning direction,
wherein, in the removing stripe-shaped tailing, tailing determination processing is performed in which a pixel value of the target pixel is compared with pixel values of upper and lower pixels adjacent to the target pixel in the sub-scanning direction, and the target pixel is determined to be a tailing pixel forming the tailing in a case where the pixel value of the target pixel is higher than the pixel values of the upper and lower pixels and a difference or a ratio between the pixel value of the target pixel and the pixel values of the upper and lower pixels is equal to or greater than a predetermined value.

* * * * *